United States Patent
Zhou et al.

(10) Patent No.: US 10,869,926 B2
(45) Date of Patent: Dec. 22, 2020

(54) SUPPRESSION OF MYELOID DERIVED SUPPRESSOR CELLS AND IMMUNE CHECKPOINT BLOCKADE

(71) Applicant: The Johns Hopkins University, Baltimore, MD (US)

(72) Inventors: Shibin Zhou, Owings Mills, MD (US); Bert Vogelstein, Baltimore, MD (US); Kenneth W. Kinzler, Baltimore, MD (US); KiBem Kim, Lutherville, MD (US)

(73) Assignee: The Johns Hopkins University, Baltimore, MD (US)

( * ) Notice: Subject to any disclaimer, the term of this patent is extended or adjusted under 35 U.S.C. 154(b) by 264 days.

(21) Appl. No.: 15/326,186

(22) PCT Filed: Jul. 13, 2015

(86) PCT No.: PCT/US2015/040107
§ 371 (c)(1),
(2) Date: Jan. 13, 2017

(87) PCT Pub. No.: WO2016/010879
PCT Pub. Date: Jan. 21, 2016

(65) Prior Publication Data
US 2017/0189526 A1 Jul. 6, 2017

Related U.S. Application Data

(60) Provisional application No. 62/069,881, filed on Oct. 29, 2014, provisional application No. 62/024,731, filed on Jul. 15, 2014.

(51) Int. Cl.
*A61K 39/395* (2006.01)
*A61K 31/437* (2006.01)
*A61K 31/00* (2006.01)
*A61K 31/706* (2006.01)
*A61K 31/4406* (2006.01)
*C07K 16/28* (2006.01)
*A61K 45/06* (2006.01)
*A61K 35/742* (2015.01)
*A61K 39/00* (2006.01)

(52) U.S. Cl.
CPC ...... *A61K 39/39558* (2013.01); *A61K 31/437* (2013.01); *A61K 31/4406* (2013.01); *A61K 31/706* (2013.01); *A61K 35/742* (2013.01); *A61K 39/3955* (2013.01); *A61K 45/06* (2013.01); *C07K 16/2818* (2013.01); *A61K 2039/505* (2013.01); *C07K 2317/34* (2013.01); *C07K 2317/92* (2013.01)

(58) Field of Classification Search
CPC ..... A61K 39/395; A61K 31/437; A61K 31/00

USPC ....................................................... 424/139.1
See application file for complete search history.

(56) References Cited

U.S. PATENT DOCUMENTS

2005/0079157 A1   4/2005   Dang et al.

FOREIGN PATENT DOCUMENTS

| WO | WO 2006/121168 | 11/2006 |
| WO | WO 2013/134467 | 9/2013 |
| WO | WO 2014/134355 | 9/2014 |
| WO | WO 2016/010879 | 1/2016 |

OTHER PUBLICATIONS

Maletzki et al. (World J Gastroenterol, Jul. 28, 2010, 16(28): 3546-3552).*
Korman AJ, Peggs KS, & Allison JP (2006) Checkpoint blockade in cancer innmmotherapy. Advances in immunology 90:297-339.
Pentcheva-Hoang T, Corse E, & Allison JP (2009) Negative regulators of T-cell activation: potential targets for therapeutic intervention in cancer, autoimmune disease, and persistent infections. Innmmol Rev 229(1):67-87 (abstract only).
Nagaraj S, Youn JI, & Gab Iilovich DI (2013) Reciprocal relationship between myeloid-derived suppressor cells and Tcells. JInnmmol 191(1):17-23.
Chen L & Flies DB (2013) Molecular mechanisms of T cell co-stimulation and coinhibition. Nature reviews. Immunology 13(4):227-242.
Talmadge JE & Gabrilovich DI (2013) History of myeloid-derived suppressor cells. Nat Rev Cancer 13(10):739-752.
Lippitz BE (2013) Cytokine patterns in patients with cancer: a systematic review. Lancet Oncol 14(6):e218-228.

(Continued)

*Primary Examiner* — Yan Xiao
(74) *Attorney, Agent, or Firm* — Fish & Richardson P.C.

(57) ABSTRACT

Impressive responses have been observed in patients treated with checkpoint inhibitory anti-PD-1 or anti-CTLA-4 antibodies. However, immunotherapy against poorly immunogenic cancers remains a challenge. Treatment with both anti-PD-1 and anti-CTLA-4 antibodies were unable to eradicate large, modestly immunogenic CT26 tumors or metastatic 4T1 tumors. However, co-treatment with epigenetic modulating drugs and checkpoint inhibitors markedly improved treatment outcomes, curing more than 80% of them. Functional studies revealed that the primary targets of the epigenetic modulators were myeloid-derived suppressor cells (MDSCs). A PI3K-inhibitor that reduced circulating MDSCs also cured 80% of mice with metastatic 4T1 tumors when combined with immune checkpoint inhibitors. Thus, cancers resistant to immune checkpoint blockade can be cured by eliminating MDSCs.

4 Claims, 9 Drawing Sheets
Specification includes a Sequence Listing.

(56) References Cited

OTHER PUBLICATIONS

Zou W (2006) Regulatory T cells, tumour immunity and immunotherapy. Nature reviews. Immunology 6(4):295-307.
Hodi FS, et al (2010) Improved survival with ipilimumab in patients with metastatic melanoma. N Engl J Med 363(8):711-723.
Topalian SL, et al (2012) Safety, activity, and immune con-elates ofanti-PD-1 antibody in cancer. N Engl J Med 366(26):2443-2454.
Brahmer JR, et al (2012) Safety and activity of anti-PD-L1 antibody in patients with advanced cancer. N Engl J Med 366(26):2455-2465.
Wolchok JD, et al (2013) Nivolumab plus ipilimumab in advanced melanoma. N Engl J Med 369(2):122-133.
Corbett TH, Griswold DP, Jr., Roberts BJ, Peckham JC, & Schabel FM, Jr. (1975) Tumor induction relationships in development of transplantable cancers of the colon in mice for chemotherapy assays, with a note on carcinogen structure. Cancer Res 35(9):2434-2439.
Belnap LP, Cleveland PH, Cohnerauer ME, Barone RM, & Pilch YH (1979) Innmmogeocity of chemically induced murine colon cancers. Cancer Res 39(4):1174-1179.
Dexter DL, et al (1978) Heterogeneityoftmnor cells from a single mouse mammaly tumor. Cancer Res 38(10):3174-3181.
Pulaski BA & Ostrand-Rosenberg S (1998) Reduction of established spontaneous mammary carcinoma metastases following immunotherapy with major histocompatibility complex class II and B7.1 cell-based tumor vaccines. Cancer Res 58(7):1486-1493.
Segal NH, et al (2008) Epitope landscape in breast and colorectalcancer. Cancer Res 68(3):889-892.
Vogelstein B, et al (2013) Cancer genome landscapes. Science 339(6127):1546-1558.
Rashid OM, et al (2013) Resection of the primary tumor improves survival in metastatic breast cancer by reducing overall tumor burden Surgery 153( 6):771-778.
Lampen MH & van Hall T (2011) Strategies to counteract MHC-I defects in tumors. Current opinion in immunology 23(2):293-298 (Abstract only).
Ostrand-Rosenberg S & Sinha P (2009) Myeloid-derived suppressor cells. linking inflammation and cancer. J Immnnol 182(8):4499-4506.
Gabrilovich DI, Ostrand-Rosenberg S, & Bronte V (2012) Coordinated regulation of myeloid cells by tumors. Nature reviews. Innmmology 12( 4 ):253-268.
Couper KN, et al (2009) Anti-CD25 antibody-mediated depletion of effector T cell populations enhances susceptibility of mice to acute but not chronic Toxoplasma gondii infection J Innmmol 182(7):3985-3994.
Setiady et al. (2010) In vivo depletion of CD4+FOXP3+ Treg cells by the PC6 1 anti-CD25 monoclonal antibody is mediated by FcyRIII+ phagocytes. Eur J Immnnol 40(3):780-786.
Srivastava MK, et al (2012) Myeloid suppressor cell depletion augments antitmnor Activity in lungcancer. PLoS One 7(7):e40677.
Schmid MC, et al (2011) Receptor tyrosine kinases and TLRIILIRs nnexpectedly activate myeloid cell PI3kgamma, a single convergent point promoting tmnor inflammation and progression CancerCell 19(6):715-727.
Schmidt-Kittler et al (PI3Kalpha inhibitors that inhibit metastasis. Oocotarget 1 (5):339-348 (2010).
Mandelker D, et al (2009) A frequent kinase domain mutation that changes the interaction between PB Kalp ha and the membrane. Proc Natl Acad Sci U S A 106( 40):16996-17001.
Zheng Z, et al (2012) Definition of the binding mode of a new class of phosphoinosit:ide 3-kinase alpha-selective inhibitors using in vitro mutagenesis of nonconserved amino acids and kinetic analysis. Biochem J 444(3):529-535.
Dokmanovic M, Clarke C, & Marks PA (2007) Histone deacetylase inhibitors: overview and perspectives. Mol Cancer Res 5(10):981-989.
Khan 0 & La Thangue NB (2012) HDAC inlnbitors in cancer biology: emerging mechanisms and clinical applications. Immunology and cell biology 90(1):85-94.

Lyko F & Brown R (2005) DNA methyltransferase inhibitors and the development of epigenetic cancer therapies. J Natl Cancer Inst 97(20):1498-1506.
Griffiths EA & Gore SD (2008) DNA methyltransrerase and histone deacetylase inhibitorsin the treatment of myelodysplastic syndromes. Sem:inHemato145(1):23-30.
Baylin SB & Jones PA (2011) A decade of exploring the cancer epigenome—biological and translational implications. Nat Rev Cancer 11(10):726-734.
Juergens RA, et al (2011) Combination epigenetic therapy has efficacy in patients with refractory advanced non-small cell lung cancer. Cancer Discov 1(7):598-607.
Pulaski et al., "Mouse 4T1 breast tumor model." Curr Protoc Immunol. May 2001;Chapter 20:Unit 20.2.
Youn et al., "Characterization of the nature of granulocytic myeloid-derived suppressor cells in tumor-bearing mice," Journal of leukocyte biology. 2012;91:167-81.
Hamilton et al., "Serum inhibits the immunosuppressive function of myeloid-derived suppressor cells isolated from 4T1 tumor-bearing mice" Cancer: immunology, immunotherapy: CII. 2012;61:643-54.
View of NCT01928576 on Aug. 23, 2013, ClinicalTrials.gov archive, Aug. 23, 2013, URL, https://clinicaltrials.gov/archive/NCT01928576/2013_08_23.
Dang, L.H. et al., Combination bacteriolytic therapy for the treatment of experimental tumors., Proc. Natl. Acad. Sci. USA, Dec. 18, 2001, vol. 98, No. 26, p. 15155-60.
Japanese Office Action for Japanese Patent Application No. 2017-502263, dated Nov. 8, 2017.
John Wrangle et al: Abstract 4619: Epigenetic therapy and sensitization of lung cancer to immunotherapy. Proceedings: AACR 104th Annual Meeting 2013 Cancer Research, vol. 73, No. 8 supp, Apr. 6, 2013.
Ordentlich P et al: "The Isoform Selective Histone Deacetylase Inhibitor Entinostat is Active in Primary Human Triple-Negative Breast Cancer Models",Cancer Research; 32nd Annual San Antonio Breast Cancer Symposium, AACR—American Association for Cancer Research, US; San Antonio, TX, USA, vol. 69, No. 24, Suppl. 3, Dec. 15, 2009.
Allard et al., "Targeting CD73 Enhances the Antitumor Activity of Anti-PD-1 and Anti-CTLA-4 mAbs," Clinical Cancer Research, vol. 19, No. 20, Oct. 15, 2013, pp. 5626-5635.
Marianne Davies: "New modalities of cancer treatment for NSCLC: focus on immunotherapy," Cancer Management and Research, Feb. 1, 2014, p. 63-75.
Stresemann et al., "Functional diversity if DNA methyltransferase inhibitors in human cancer cell lines," Cancer Research, AACR, vol. 66, No. 5, Mar. 1, 2006, pp. 2794-2800.
Satbir Thakur et al., ING1 and 5-Azacytidine Act Synergistically to Block Breast Cancer Cell Growth, PLOS ONE, vol. 7, No. 8, Aug. 20, 2012, p. e43671.
Bracker Tomke Ute et al., "Efficacy of MS-275, a selective inhibitor of class I histone deacetylases, in human colon cancer models," International Journal of Onco, Spandidos: Athens, GR, vol. 35, No. 4, Oct. 1, 2009, pp. 909-920.
Supplementary European Search Report issued in European Application No. 15822398.2, dated Nov. 30, 2017, 21 pages.
Wrangle, J, et al. 'Alterations of Immune Response of Non-Small Cell Lung Cancer with Azacytidine', Oncotarget, 2013, vol. 4, No. 11, pp. 2067-2079.
Curran, M, A. et al., 'PD-1 and CTLA-4 combination blockade expands infiltrating T cells and reduces regulatory T and myeloid cells within B16 melanoma tumors', Proceedings of the National Academy of Sciences, 2010, vol. 107, No. 9, pp. 4276-4280.
Mikyskova, R. et al., 'DNA demethylating agent 5-azacytidine inhibits myeloid-derived suppressor cells induced by tumor growth and cyclophosphamide treatment', Journal of Leukocyte Biology, May 2014, vol. 95, pp. 743-753.
International Search Report for PCT/US2015/040107 (dated Sep. 25, 2015) prepared by ISA-KR.
Belinsky, S. A., et al., 'Combination therapy with vidaza and entinostat suppresses tumor growth and reprograms he epigenome in an orthotopic lung cancer model', Cancer Research, 2011, vol. 71, No. 2, pp. 454-462.

(56) References Cited

OTHER PUBLICATIONS

Pardoll, D. M., 'The blockade of immune checkpoints in cancer immunotherapy', Nature Reviews Cancer, 2012, vol. 12, Issue 4, pp. 252-264.

Bio-Rad Laboratories, Inc., The Role of Immune Checkpoints in Immunity and Cancer (online) retrieved on 2019 Jun. 14, 2017, p. 1-8, retrieved from the Internet <URL:http://www.bio-rad-antibodies.com/static/2017/innate/the-role-of-immune-checkpoints-in-immunity-and-cancer.pdf>.

Rosborough et al., "Histone deacetylase inhibition facilitates GM-CSF-mediated expansion of myeloid derived suppressor cells in vitro and in vivo", Journal of leukocyte Biology, 91, p. 701-709, 2012.

\* cited by examiner

SEQUENCE LISTING

<160> NUMBER OF SEQ ID NOS: 37

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
agggcaatga gcagagtttc                                               20

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
ccacgttttc aggtcttcgt                                               20

<210> SEQ ID NO 3
<211> LENGTH: 20
<212> TYPE: DNA
<213> ORGANISM: Artificial Sequence
<220> FEATURE:
<223> OTHER INFORMATION: PCR primer

<400> SEQUENCE: 3 attcacccccc actgagactg                                              20

<210> SEQ ID NO 4
<211> LENGTH: 21
<212> TYPE: DNA
<213> ORGANISM: Artificial Sequence
<220> FEATURE:
<223> OTHER INFORMATION: PCR primer

<400> SEQUENCE: 4
gctatttctt tctgcgtgca t                                             21

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
gagacatgct gtgtcggatg                                               20

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
tggtgagaat ggacatgagc                                               20

-continued

<210> SEQ ID NO 7
<211> LENGTH: 24
<212> TYPE: DNA
<213> ORGANISM: Artificial Sequence
<220> FEATURE:
<223> OTHER INFORMATION: PCR primer

<400> SEQUENCE: 7
ttctttgcag ctccttcgtt gccg                                          24

<210> SEQ ID NO 8
<211> LENGTH: 24
<212> TYPE: DNA
<213> ORGANISM: Artificial Sequence
<220> FEATURE:
<223> OTHER INFORMATION: PCR primer

<400> SEQUENCE: 8
tggatggcta cgtacatggc tggg                                          24

<210> SEQ ID NO 9
<211> LENGTH: 9
<212> TYPE: PRT
<213> ORGANISM: Homo sapiens

<400> SEQUENCE: 9

Ser Gly Pro Ser Tyr Ala Thr Tyr Leu
1               5

<210> SEQ ID NO 10
<211> LENGTH: 9
<212> TYPE: PRT
<213> ORGANISM: Homo sapiens

<400> SEQUENCE: 10

Ser Tyr Glu Thr Leu Lys Lys Ser Leu
1               5

<210> SEQ ID NO 11
<211> LENGTH: 9
<212> TYPE: PRT
<213> ORGANISM: Homo sapiens

<400> SEQUENCE: 11

Ser Tyr Thr Ser Tyr Ile Met Ala Ile
1               5

<210> SEQ ID NO 12
<211> LENGTH: 9
<212> TYPE: PRT
<213> ORGANISM: Homo sapiens

<400> SEQUENCE: 12

Arg Tyr Trp Thr Gly Ile Gly Val Leu
1               5

<210> SEQ ID NO 13
<211> LENGTH: 9
<212> TYPE: PRT
<213> ORGANISM: Homo sapiens

<400> SEQUENCE: 13

Ala Tyr Val Asn Ala Ile Glu Lys Ile
1               5

```
<210> SEQ ID NO 14
<211> LENGTH: 9
<212> TYPE: PRT
<213> ORGANISM: Homo sapiens

<400> SEQUENCE: 14

Ser Tyr Ile Lys Lys Leu Lys Glu Leu
1               5

<210> SEQ ID NO 15
<211> LENGTH: 9
<212> TYPE: PRT
<213> ORGANISM: Homo sapiens

<400> SEQUENCE: 15

His Tyr Leu Asn Asp Gly Asp Ala Ile
1               5

<210> SEQ ID NO 16
<211> LENGTH: 9
<212> TYPE: PRT
<213> ORGANISM: Homo sapiens

<400> SEQUENCE: 16

Lys Val Leu Ala Gly Lys Ser Thr Ile
1               5

<210> SEQ ID NO 17
<211> LENGTH: 9
<212> TYPE: PRT
<213> ORGANISM: Homo sapiens

<400> SEQUENCE: 17

His His Thr Met Met Val Gln Ala Ile
1               5

<210> SEQ ID NO 18
<211> LENGTH: 9
<212> TYPE: PRT
<213> ORGANISM: Homo sapiens

<400> SEQUENCE: 18

Ala Tyr Ala Leu Asn Arg Arg Asn Leu
1               5

<210> SEQ ID NO 19
<211> LENGTH: 9
<212> TYPE: PRT
<213> ORGANISM: Homo sapiens

<400> SEQUENCE: 19

Ser Tyr Ile Met Ala Ile Cys Gly Met
1               5

<210> SEQ ID NO 20
<211> LENGTH: 9
<212> TYPE: PRT
<213> ORGANISM: Homo sapiens

<400> SEQUENCE: 20

Tyr Tyr Met Arg Asp Val Ile Ala Ile
1               5

<210> SEQ ID NO 21
```

```
<211> LENGTH: 9
<212> TYPE: PRT
<213> ORGANISM: Homo sapiens

<400> SEQUENCE: 21

Leu Phe Leu Lys Ser Pro Thr Ala Leu
1               5

<210> SEQ ID NO 22
<211> LENGTH: 9
<212> TYPE: PRT
<213> ORGANISM: Homo sapiens

<400> SEQUENCE: 22

Pro Tyr Phe Arg Leu Glu His Tyr Leu
1               5

<210> SEQ ID NO 23
<211> LENGTH: 9
<212> TYPE: PRT
<213> ORGANISM: Homo sapiens

<400> SEQUENCE: 23

Ser Tyr Leu Arg Arg Leu Pro Gly Leu
1               5

<210> SEQ ID NO 24
<211> LENGTH: 9
<212> TYPE: PRT
<213> ORGANISM: Homo sapiens

<400> SEQUENCE: 24

Thr Tyr Trp Lys Gly Asn Pro Glu Met
1               5

<210> SEQ ID NO 25
<211> LENGTH: 9
<212> TYPE: PRT
<213> ORGANISM: Homo sapiens

<400> SEQUENCE: 25

Gly Tyr Glu Ala Val Val Arg Leu Leu
1               5

<210> SEQ ID NO 26
<211> LENGTH: 9
<212> TYPE: PRT
<213> ORGANISM: Homo sapiens

<400> SEQUENCE: 26

Pro Tyr Leu Thr Ala Leu Asp Asp Leu
1               5

<210> SEQ ID NO 27
<211> LENGTH: 9
<212> TYPE: PRT
<213> ORGANISM: Homo sapiens

<400> SEQUENCE: 27

Leu Phe Val Thr Val Leu Glu Val Ile
1               5

<210> SEQ ID NO 28
<211> LENGTH: 9
<212> TYPE: PRT
```

<213> ORGANISM: Homo sapiens

<400> SEQUENCE: 28

Val Tyr Phe Thr Ile Asn Val Asn Leu
1               5

<210> SEQ ID NO 29
<211> LENGTH: 9
<212> TYPE: PRT
<213> ORGANISM: Homo sapiens

<400> SEQUENCE: 29

Ser Tyr Thr Glu Gln Asn Val Lys Leu
1               5

<210> SEQ ID NO 30
<211> LENGTH: 9
<212> TYPE: PRT
<213> ORGANISM: Homo sapiens

<400> SEQUENCE: 30

Phe Tyr Thr Ser Tyr Leu Arg Arg Leu
1               5

<210> SEQ ID NO 31
<211> LENGTH: 9
<212> TYPE: PRT
<213> ORGANISM: Homo sapiens

<400> SEQUENCE: 31

Phe Pro Pro Gln Asn Met Phe Glu Phe
1               5

<210> SEQ ID NO 32
<211> LENGTH: 9
<212> TYPE: PRT
<213> ORGANISM: Homo sapiens

<400> SEQUENCE: 32

Ser Pro Glu Ala Gln Leu Phe Ala Val
1               5

<210> SEQ ID NO 33
<211> LENGTH: 9
<212> TYPE: PRT
<213> ORGANISM: Homo sapiens

<400> SEQUENCE: 33

Glu Pro Gln Ile Ala Met Asp Asp Met
1               5

<210> SEQ ID NO 34
<211> LENGTH: 9
<212> TYPE: PRT
<213> ORGANISM: Homo sapiens

<400> SEQUENCE: 34

Ile Pro Asp Glu Ala Met Val Lys Leu
1               5

```
<210> SEQ ID NO 35
<211> LENGTH: 9
<212> TYPE: PRT
<213> ORGANISM: Homo sapiens

<400> SEQUENCE: 35

Glu Pro Gln Val Glu Pro Leu Asp Phe
1               5

<210> SEQ ID NO 36
<211> LENGTH: 9
<212> TYPE: PRT
<213> ORGANISM: Homo sapiens

<400> SEQUENCE: 36

Asp Pro Phe Ala Thr Pro Leu Ser Met
1               5

<210> SEQ ID NO 37
<211> LENGTH: 9
<212> TYPE: PRT
<213> ORGANISM: Homo sapiens

<400> SEQUENCE: 37

Phe Pro Pro Asp Ala Ile Asn Asn Phe
1               5
```

SUPPRESSION OF MYELOID DERIVED SUPPRESSOR CELLS AND IMMUNE CHECKPOINT BLOCKADE

STATEMENT OF FEDERALLY SPONSORED RESEARCH

This invention was made with government support under grants CA043460 and CA062924 awarded by the National Institutes of Health. The government has certain rights in the invention.

TECHNICAL FIELD OF THE INVENTION

This invention is related to the area of cancer treatment. In particular, it relates to combination therapies to overcome treatment refractory tumors.

BACKGROUND OF THE INVENTION

The mammalian immune system is delicately regulated, allowing it to mount an effective attack against foreign invaders such as bacteria and viruses with minimal bystander casualties. This requires functionally redundant regulatory mechanisms to ensure safety (1-3). Cancers appear able to hijack these mechanisms to avoid immune destruction. Several of the regulatory mechanisms exploited by cancer have been identified. These include regulatory T cells (Tregs), circulating MDSCs, resident tumor-associated macrophages and neutrophils, checkpoint inhibiting receptors on T-cells, and immunosuppressive cytokines (4-8). Most recently, the checkpoints guarded by the PD-1 and CTLA-4 receptors have been under intense investigation because of the availability of antibodies which can inhibit their function. Recent clinical trials with anti-CTLA-4, anti-PD-1 and anti-PD-L1 monoclonal antibodies (mAbs) showed remarkable therapeutic responses (9-12), underscoring the idea that disruption of the immune checkpoints can be therapeutically useful. Yet, the objective responses were observed in a minority of the treated patients and tumor types, and the reasons why certain tumors respond and others don't are mysterious. CT26 and 4T1 are among the most popular syngeneic tumor models used for assessing novel therapeutic approaches. CT26 was derived from an undifferentiated colorectal carcinoma induced in a BALB/c mouse by repeated intrarectal instillations of N-nitroso-N-methylurethan and shown to be modestly immunogenic (13, 14), whereas 4T1 originated from a spontaneous mammary tumor in a BALB/c mouse (15). 4T1 is poorly immunogenic and highly metastatic, characteristics shared with advanced human cancers (16). Despite the extensive use of these tumor cell lines in cancer research, little genetic characterization is available for either of them.

There is a continuing need in the art to overcome the problem of treatment recalcitrant cancers so that remissions may be longer lasting and more widely spread in the population treated.

SUMMARY OF THE INVENTION

According to one aspect of the invention a method of treating a tumor-bearing mammal is provided. At least one first agent which suppresses myeloid derived suppressor cells (MDSCs) is administered to the mammal. At least one second agent which blocks an immune checkpoint is administered to the mammal. The tumor may or may not be non-small cell lung cancer (NSLC).

According to another aspect of the invention a kit is provided. The kit comprises a single package and contains at least one first agent which suppresses myeloid derived suppressor cells (MDSCs). It further contains at least two second agents which block at least two immune checkpoints.

In yet another aspect of the invention a composition is provided. The composition comprises at least one first agent which suppresses myeloid derived suppressor cells (MDSCs) and at least two second agents which block at least two immune checkpoints.

According to another aspect of the invention a method of treating a tumor-bearing mammal is provided. At least one first agent which suppresses myeloid derived suppressor cells (MDSCs) is administered to the mammal. At least two second agents which block at least two immune checkpoints are administered to the mammal.

In yet another aspect of the invention a method of treating a mammal with a bacterial or viral infection is provided. At least one agent which suppresses myeloid derived suppressor cells (MDSCs) is administered. The agent is selected from the group consisting of a histone deacetylase inhibitor, a DNA methyltransferase inhibitor, a p110α subunit of phosphoinositol 3 kinase (PI3K) inhibitor, and combinations thereof.

These and other embodiments which will be apparent to those of skill in the art upon reading the specification provide the art with therapeutic preparations and methods for treating hard to treat tumors.

BRIEF DESCRIPTION OF THE DRAWINGS

(FIG. 1A and FIG. 1B) BALB/c mice with CT26 tumors of moderate sizes. (FIG. 1C and FIG. 1D) BALB/c mice with large CT26 tumors. (FIG. 1E and FIG. 1F) BALB/c mice with metastatic 4T1 tumors. (FIG. 1G) 4T1 tumor-bearing mice were treated as indicated and euthanized six weeks after tumor implantation. Primary tumor from each mouse was measured and metastatic lesions (mets) lesions in different organs were counted. Means and standard deviations are shown. Number (n) of animals used in each experimental arm and P-values are also indicated. * $P<0.05$,  $P<0.01$, * $P<0.001$, ns, not significant.

(FIG. 2A) FACS result for tumor-infiltrating $CD8^+$ T cells. (FIG. 2B) Representative immunohistofluorescent staining of tumor-infiltrating $CD8^+$ T cells. Scale bar, 50 μm (FIG. 2C) FACS result for tumor-infiltrating $CD4^+CD25^+FoxP3^+$ Tregs. (FIG. 2D) Representative FACS data showing percentages of FoxP3 and CD25 double positive cells in $CD45^+CD3^+CD4^+$ gated tumor-infiltrating cells. (FIG. 2E) FACS result for circulating G-MDSCs. (F) Representative FACS data showing percentages of $Ly6G^+Ly6C^{lo}$ cells in $CD45^+CD11b^+F4/80^-MHC\text{-}II^-$ gated circulating cells. (FIG. 2G) FACS result for tumor-infiltrating G-MDSCs. (FIG. 2H)

Representative immunohistofluorescent staining of tumor-infiltrating Ly6G$^+$ cells. Scale bar, 50 μm.

Figures 3A, 3B, 3C:
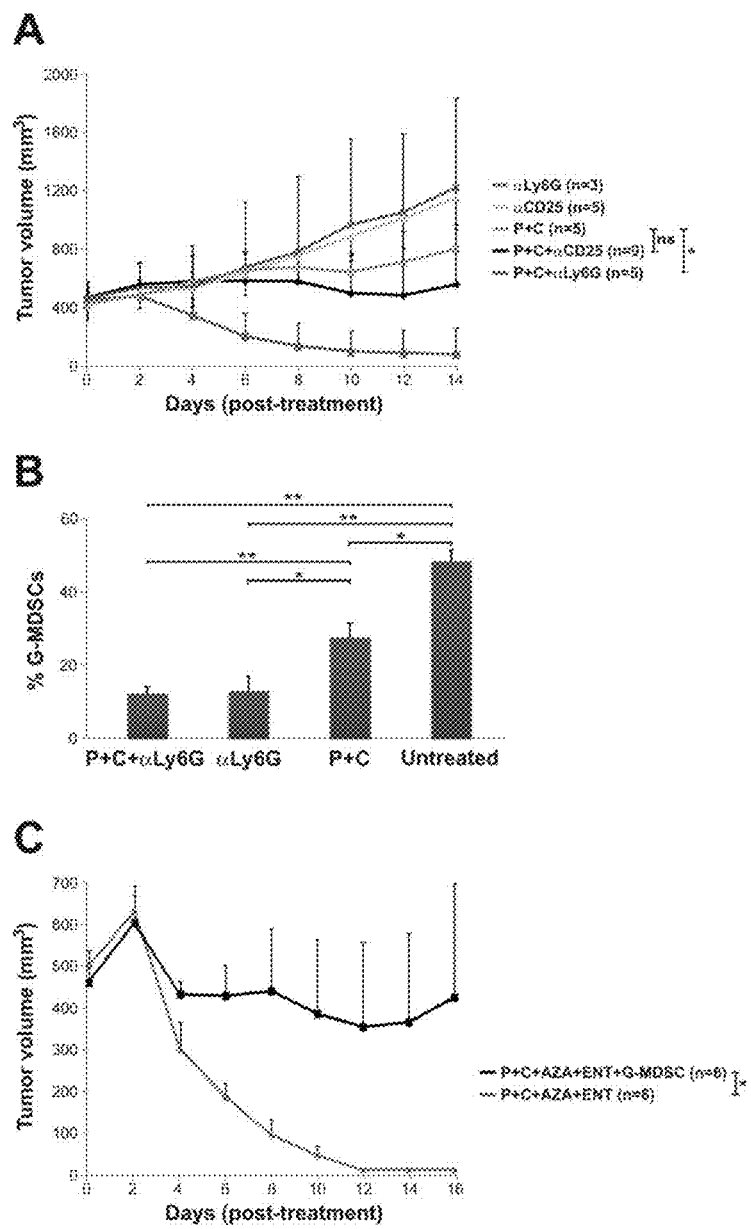

FIGS. 3A-3C. Myeloid-derived Ly6G$^+$ cells are responsible for resistance to immune checkpoint blockade. (FIG. 3A) BALB/c mice bearing 4T1 tumors were treated with various antibodies or antibody combinations as indicated and tumor volumes recorded over time. αLy6G, anti-Ly6G antibody; αCD25, anti-CD25 antibody. (FIG. 3B) FACS result for circulating G-MDSCs after treatment with different antibodies or antibody combinations. (FIG. 3C) 4T1 tumor-bearing mice were treated with anti-PD-1/anti-CTLA-4 antibodies plus epigenetic modulators with or without adoptive transfer of MDSCs isolated by affinity purification from the 4T1 tumor-bearing animals. Tumor volumes were recorded following the treatments. Means and standard deviations are shown, with P-values indicated.

Figures 4A, 4B, 4C, 4D:
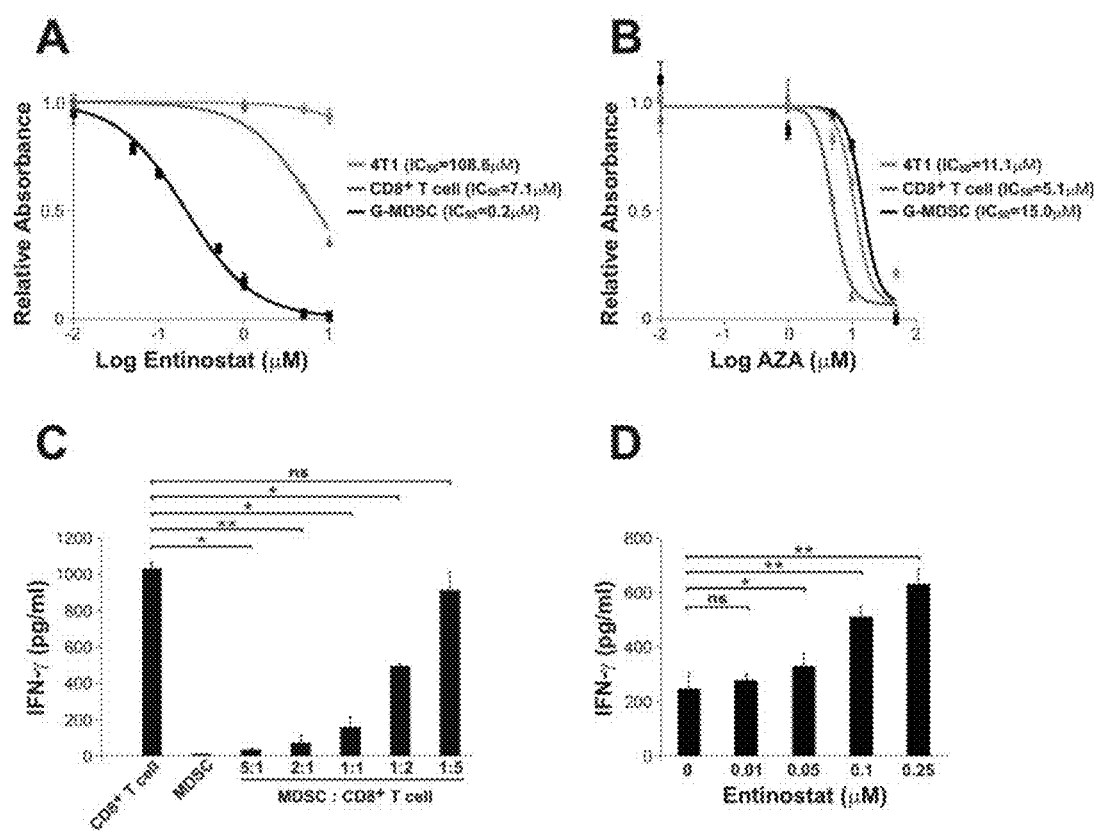

FIGS. 4A-4D. Direct effects of epigenetic modulators on cultured cells. (FIG. 4A and FIG. 4B) 4T1 cells, purified CD8$^+$ T cells or G-MDSCs were treated with different concentrations of entinostat (FIG. 4A) or AZA (FIG. 4B). Cell viability was assessed using a metabolism-based colotimetric assay. (FIG. 4C) Conditioned media from co-cultures of G-MDSCs and CD8$^+$ T cells at different ratios were analyzed for IFN-γ concentration. (FIG. 4D) Conditioned media from co-cultures at a G-MDSC to CD8$^+$ T cell ratio of 1:1 were collected after treatment with entinostat at increasing doses for 24 hours and analyzed for IFN-γ concentration Means and standard deviations of data from at least triplicate wells are shown. P-values are indicated.

Figure 5:
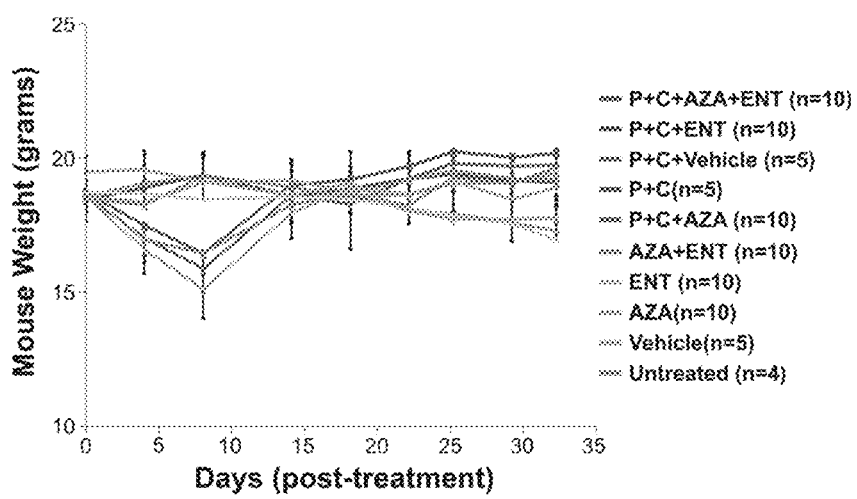

FIG. 5 (S1). Body weight measurements. BALB/c mice bearing 4T1 tumors were treated with indicated therapeutic modalities. Their body weights were measured and recorded regularly after treatments. Means and standard deviations of data are shown.

Figure 6:
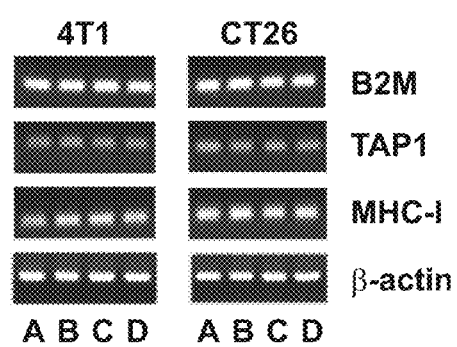

FIG. 6 (S2). Expression of genes involved in MHC-I presentation. RNA was isolated from 4T1 and CT26 tumor cells cultured in vitro after treatment with the epigenetic modulators. The expression of different genes involved in MHC-I presentation was assessed by RT-PCR. β-actin was used as loading control. Lane A, untreated, Lane B, AZA treated, Lane C, entinostat treated, Lane D, AZA/entinostat treated.

Figures 7A, 7B:
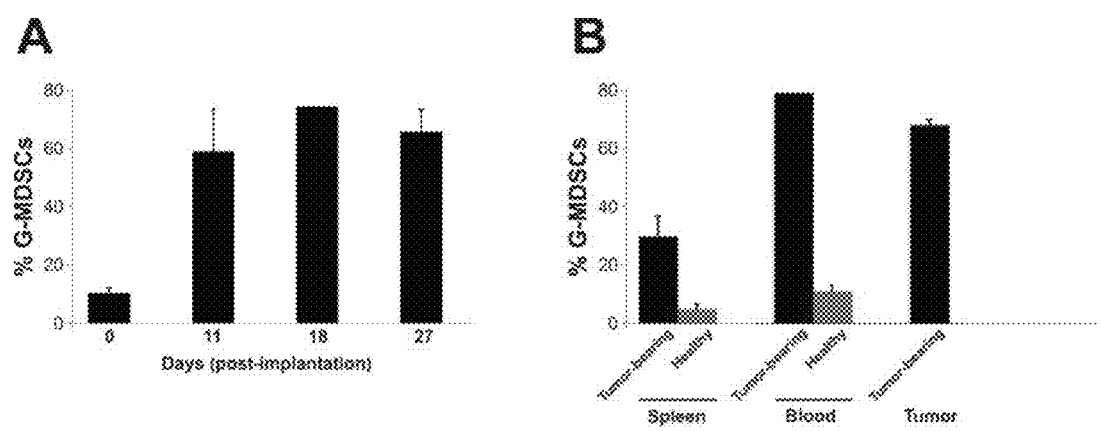

FIGS. 7A-7B. (S3). Elevated G-MDSC levels induced by 4T1 tumor. (FIG. 7A) Peripheral blood was collected at indicated time points after 4T1 tumor implantation and analyzed for the levels of G-MDSCs by FACS. (FIG. 7B) Peripheral blood, spleen, and tumor were harvested from healthy mice or from tumor-bearing mice on day 18 after 4T1 tumor implantation and analyzed for the levels of G-MDSCs by FACS. Means and standard deviations of data are shown.

Figures 8A, 8B, 8C:
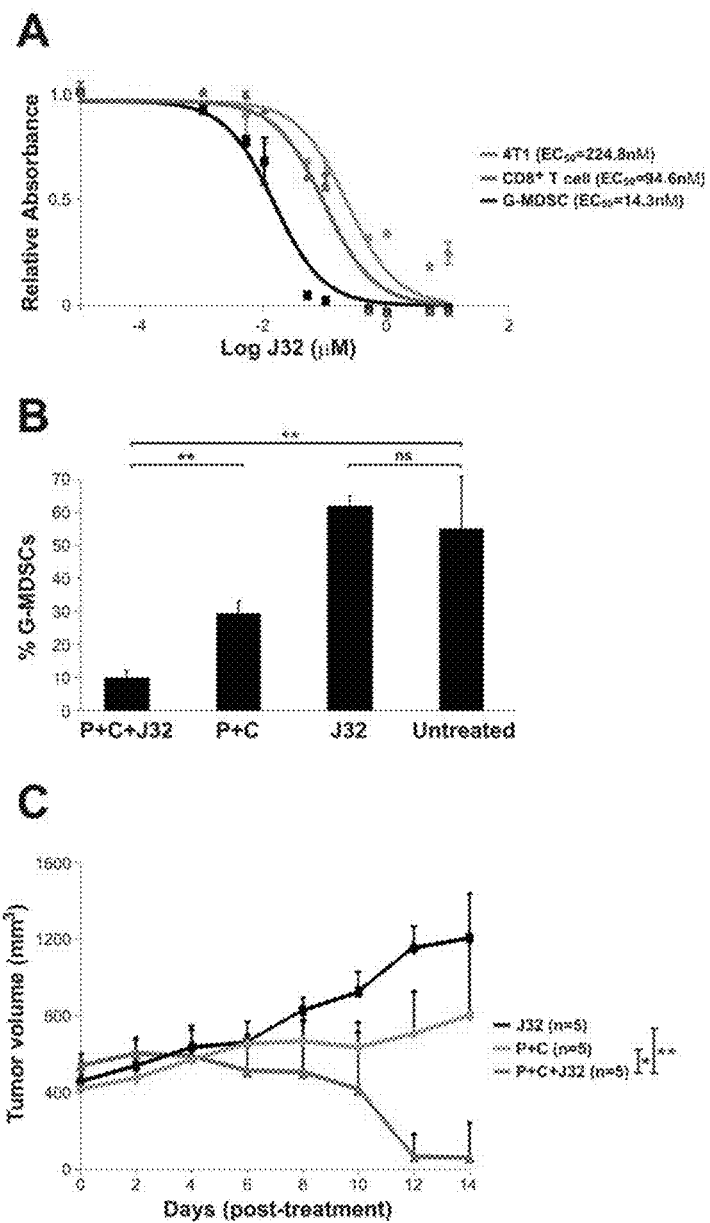

FIGS. 8A-8C (S4). PI3K inhibitor eradicates 4T1 tumor by depleting G-MDSC when combined with immune checkpoint blockade. (FIG. 8A) G-MDSCs, CD8$^+$ T cells and 4T1 tumor cells were treated in vitro with J32 at various concentrations. Cell viability was assessed using a metabolism-based colorimetric assay. Means and standard deviations of data from triplicate wells are shown. (FIG. 8B) BALB/c mice bearing 4T1 tumors were treated with indicated therapeutic modalities. FACS analysis was performed to quantify circulating G-MDSCs. (FIG. 8C) BALB/c mice bearing 4T1 tumors were treated with J32, anti-PD-1/anti-CTLA-4 antibodies or the combination and tumor volumes recorded. Means and standard deviations are shown, with P-values indicated.

Figure 9:
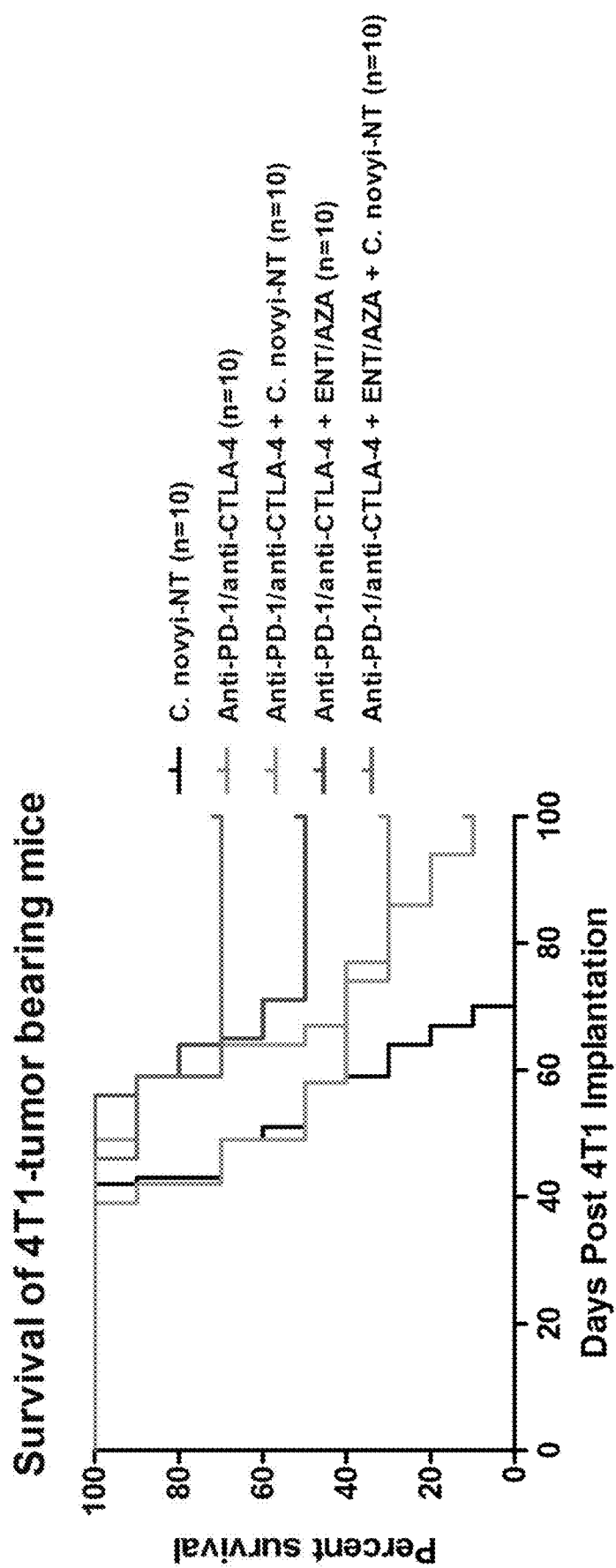

FIG. 9. Meier Kaplan curves for combination treatments. From lowest to highest curves: *C. novyi*-NT alone; Anti-PD-1/anti-CTLA-4 alone; Anti-PD-1/anti-CTLA-4+*C. novyi*-NT; Anti-PD-1/anti-CTLA-4+ENT/AZA; Anti-PD-1/anti-CTLA-4+ENT/AZA+*C. novyi*-NT.

DETAILED DESCRIPTION OF THE INVENTION

The inventors have developed a therapeutic approach that involves agents that act on host cells in the immune system such as MDSCs to reduce and/or suppress them. Such agents may be epigenetic modulators such as histone deacetylase inhibitors or DNA methyltransferase inhibitors. When used in conjunction with immune checkpoint blockade, the epigenetic modulators kill MDSCs at much lower concentrations than required for killing tumor cells in vitro. The epigenetic modulators have only a marginal effect at best on tumor cells in vivo at the doses used; reduction of MDSCs using antibodies directed against them has similar antitumor effects to those observed with the epigenetic modulators. In adoptive transfer experiments, MDSCs purified from non-treated tumor-bearing mice can abolish the therapeutic effects of epigenetic modulation. Inhibition of MDSCs with a completely different class of agents (a PIK3 inhibitor) has similar effects to those of epigenetic modulators.

Types of tumors which are amenable to treatment according to the methods of the invention and/or using the kits and/or using the compositions of the invention are both solid tumors and hematological cancers. Exemplary tumors include Adrenal Cancer, Anal Cancer, Bile Duct Cancer, Bladder Cancer, Bone Cancer, Brain/CNS Tumors In Adults, Brain/CNS Tumors In Children, Breast Cancer, Breast Cancer In Men, Cancer in Adolescents, Cancer in Children, Cancer in Young Adults, Cancer of Unknown Primary, Castleman Disease, Cervical Cancer, Colon/Rectum Cancer, Endometrial Cancer, Esophagus Cancer, Ewing Family Of Tumors, Eye Cancer, Gallbladder Cancer, Gastrointestinal Carcinoid Tumors, Gastrointestinal Stromal Tumor (GIST), Gestational Trophoblastic Disease, Hodgkin Disease, Kaposi Sarcoma, Kidney Cancer, Laryngeal and Hypopharyngeal Cancer, Leukemia, Leukemia—Acute Lymphocytic (ALL) in Adults, Leukemia—Acute Myeloid (AML), Leukemia—Chronic Lymphocytic (CLL), Leukemia—Chronic Myeloid (CML), Leukemia—Chronic Myelomonocytic (CMML), Leukemia in Children, Liver Cancer, Lung Cancer, Lung Cancer—Non-Small Cell, Lung Cancer—Small Cell, Lung Carcinoid Tumor, Lymphoma, Lymphoma of the Skin, Malignant Mesothelioma, Multiple Myeloma, Myelodysplastic Syndrome, Nasal Cavity and Paranasal Sinus Cancer, Nasopharyngeal Cancer, Neuroblastoma, Non-Hodgkin Lymphoma, Non-Hodgkin Lymphoma In Children, Oral Cavity and Oropharyngeal Cancer, Osteosarcoma, Ovarian Cancer, Pancreatic Cancer, Penile Cancer, Pituitary Tumors, Prostate Cancer, Retinoblastoma, Rhabdomyosarcoma, Salivary Gland Cancer, Sarcoma—Adult Soft Tissue Cancer, Skin Cancer, Skin Cancer—Basal and Squamous Cell, Skin Cancer—Melanoma, Skin Cancer—Merkel Cell, Small Intestine Cancer, Stomach Cancer, Testicular Cancer, Thymus Cancer, Thyroid Cancer, Uterine Sarcoma, Vaginal Cancer, Vulvar Cancer, Waldenstrom Macroglobulinemia, and Wilms Tumor.

Types of bacterial infections which can be treated according to the methods of the invention include *Bacillus anthracia, Bordetella pertussis, Borrelia burgdorferi, Brucella abortus Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens,*

*Clostridium tetani, Corynebacterium diphtheriae, Enterococcus faecalis* and *Enterococcus faecium, Escherichia coli* (generally), Enterotoxigenic *Escherichia coli* (ETEC), Enteropathogenic *E. coli, E. coli* O157:H7, *Francisella tularensis, Haemophilus influenzae, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei*, and *Staphylococcus aureus*.

Types of viral infections which can be treated according to the invention include both chronic and acute infections. Exemplary infection include Respiratory Viruses, such as, Adenoviruses, Avian influenza, Influenza virus type A, Influenza virus type B, Measles, Parainfluenza virus, Respiratory syncytial virus (RSV), Rhinoviruses, SARS-CoV Gastro-enteric Viruses, such as, Coxsackie viruses, Enteroviruses, Poliovirus, Rotavirus, Hepatitis Viruses, such as, Hepatitis B virus, Hepatitis C virus, Bovine viral diarrhea virus (surrogate), Herpes Viruses, such as, Herpes simplex 1, Herpes simplex 2, Human cytomegalovirus, Varicella zoster virus, Retroviruses, such as, Human immunodeficiency virus 1 (HIV-1), Human immunodeficiency virus 2 (HIV-2), Simian immunodeficiency virus (SIV), Simian human immunodeficiency virus (SHIV), Viral Select Agents/Emerging Viral Pathogens, such as, Avian influenza, Dengue virus, Hantavirus, Hemorrhagic fever viruses, Lymphocytic choromeningitis virus, Smallpox virus surrogates, Cowpox, Monkeypox, Rabbitpox, Vaccinia virus, Venezuelan equine encephalomyelitis virus (VEE), West Nile virus, Yellow fever virus.

Types of antibodies which may be used to target immune checkpoints or MSDCs may be of any isotype. They may be humanized or chimeric or other mammal or animal They may be conjugated to other moieties such as toxins. They may be monoclonal or polyclonal. They may be single chain antibodies, fragments, or portions of antibodies.

Modes of administration for the therapeutic agents may be those which are used in the art. Examples include oral, topical, inhalation, and injection. Locations for administration include epicutaneous or topical, nasal administration, intraarterial, intraarticular, intracardiac, intramuscular, intradermal, intralesional, intraosseous infusion, intraperitoneal, intrathecal, intrauterine, intravaginal administration, intravenous, Intravesical infusion, intravitreal, subcutaneous, transdermal, transmucosal, avitreal, subcutaneous, transdermal, and transmucosal.

Mammals which may be treated include any which are susceptible to tumors, hematological cancers, bacterial infections or viral infections. These include: Acouchi—Myoprocta acouchy (formerly, pratti), Alpaca—*Lama pacos*, Anteater, giant—*Myrmecophaga tridactyla*, Armadillo, southern (formerly La Plata) three-banded—*Tolypeutes matacus*, Banded mongoose—*Mungos mungo*, Bear, sloth—*Melursus ursinus*, Bear, Andean or spectacled—*Tremarctos ornatus*, Beaver, American—*Castor canadensis, Bison*, American—*Bison bison* (SCBI Front Royal only), *Caracal—Caracal caracal*, Cat, fishing—*Prionailurus viverrinus*, Cavy, rock—*Kerodon rupestris*, Cheetah—*Acinonyx jubatus*, Clouded leopard—*Neofelis nebulosa*, Coati—*Nasua narica, Colobus*, black-and-white or guereza—*Colobus guereza*, Cow, Hereford—*Bos taurus taurus* hereford, Cow, Holstein—*Bos taurus taurus* holstein, Deer, Burmese brow-antlered (Eld's deer)—*Cervus eldi* thamin (SCBI Front Royal only), Deer, tufted—*Elaphodus cephalophus* (SCBI Front Royal only), Degu—*Octodon degas*, Donkey, miniature—*Equus asinus asinus* miniature, Elephant, Asian—*Elephas maximus*, Elephant shrew, short-eared—*Macroscelides proboscideus*, Ferret, black-footed—*Mustela nigripes*, Gazelle, Dama—*Gazella dama*, Gibbon, white-cheeked—*Nomascus leucogenys*, Goat, Nigerian dwarf—*Capra hircus hircus* nigerian dwarf, Goat, Nubian—*Capra hircus hircus* anglo nubian, Goat, San Clemente Island—*Capra hircus hircus* san Clemente, *Gorilla*, western lowland—*Gorilla gorilla gorilla*, Hog, Ossabaw Island—*Sus scrofa scrofa*, Horse, Przewalski's—*Equus caballus przewalskii* or *Equus ferus przewalskii*, Hyrax, rock—*Procavia capensis, Lemur*, ring-tailed—*Lemur catta, Lemur*, red-fronted (subspecies of brown lemur)—*Lemur fulvus rufus, Lemur*, red-ruffed—*Varecia variegata rubra*, Lion, African—*Panthera leo leo*, Macaque, Celebes crested (formerly, Sulawesi)—*Macaca nigra*, Macaque, liontail—*Macaca silenus*, Marmoset, Geoffroy's (White-fronted or tufted-eared marmoset)—*Callithrix geoffroyi*, Meerkat—*Suricata suricatta*, Mole rat, Damaraland—*Cryptomys damarensis*, Mole-rat, Naked—*Heterocephalus glaber*, Monkey, black howler—*Alouatta caraya*, Mongoose, dwarf—*Helogale parvula*, Onager, Persian—*Equus hemionus* onager (SCBI Front Royal only), Orangutan, Bornean—*Pongo pygmaeus*, Orangutan, Suma-tran-Bornean—*Pongo pygmaeus abelii, Oryx*, scimitar-horned—*Oryx dammah*, Otter, Asian small-clawed—*Aonyx cinerea*, Otter, North American river—*Lontra* (formerly, *Lutra*) *canadensis*, Panda, giant—*Ailuropoda melanoleuca*, Panda, red—*Ailurus fulgens*, Peccary, collared—*Tayassu tajacu*, Porcupine, prehensile-tailed—*Coendou prehensilis*, Prairie dog, black-tailed—*Cynomys ludovicianus*, Rabbit, silver fox—*Oryctolagus cuniculus*, Saki, Guianan (Pale-headed saki)—*Pithecia pithecia*, Seal, gray—*Halichoerus grypus*, Siamang—*Hylobates syndactylus*, Sloth, two-toed—*Choloepus didactylus*, Squirrel, Prevost's—*Callosciurus prevosti*, Tamarin, golden lion—*Leontopithecus rosalia*, Tamarin, golden-headed lion—*Leontopithecus chrysomelas*, Tenrec, greater Madagascar—*Setifer setosus*, Tenrec, small Madagascar hedgehog—*Echinops telfairi*, Tiger, Sumatran—*Panthera tigris sumatrae, Titi*, dusky (*Orabussu titi*)—*Callicebus moloch*, Tree shrew, northern—*Tupaia belangeri*, Wolf maned—*Chrysocyon brachyurus*, and Zebra, Grevy's—*Equus grevyi*, pets, farm animals, and wild animals may be treated as well as humans.

Kits are typically a divided or undivided container that packages or contains multiple components. The components may be separated or mixed. They may agents and/or delivery devices and/or instructions. They may include mixing vessels or devices.

Spores of anaerobic *Clostridium novyi* may also be used in combination with the other agents described here. The addition of *Clostridium* spores achieves any even higher level of survival in a tumor-bearing individual, even though alone it is less effective than the other treatments. Amount of spores administered can be, for example, from $10^5$ to $10^9$, from $10^6$ to $10^8$, or from $1\times10^7$ to $10^8$ per mouse. In one embodiment the amount of spores is $5.0\times10^7$ per mouse. Balb/c mice average about 20-30 g. The amount of spores can be scaled according to body weight of the recipient.

While the precise mechanism of action of the spores is not yet known, it is known that *C. novyi*-NT infection can elicit a CD8+ T cell-mediated adaptive immune response specifically against the tumors *C. novyi*-NT has infected. Moreover, it is known that $CD8^+$ T cells from *C. novyi*-NT-cured mice can confer adoptive immunity in a tumor-specific fashion. Thus $CD8^+$ T cells are involved in the beneficial effect. See Agrawal et at, *Proc Natl Acad Sci USA*. 2004 Oct.

19; 101(42): 15172-15177. One hypothesis is that a robust inflammatory response induced by bacterial infection enhances the adaptive immune response in general (against both bacteria and tumor cells).

While applicants do not wish to be bound by any theory regarding the mechanism of action, it is reasonable to postulate that in order to generate a potent anti-tumor immune response, two important components should be in place: (a) strong tumor antigens or a robust inflammatory response to enhance the adaptive anti-tumor immune response if strong tumor antigens are not present (as can be provided by C. novyi-NT infection); and (b) cytotoxic T cells that are not inactivated by the immune checkpoints (as can be provided by anti-PD-1/anti-CTLA/4 antibody treatment) or MDSC (as can be provided by entinostat/5-azacitidine).

A recent clinical study demonstrated that epigenetic modulation exerted major therapeutic effects on a small fraction of patients with non-small cell lung cancer (NSCLC) (36). Other studies have suggested that 5-azacitidine up-regulates genes and pathways related to both innate and adaptive immunity and genes related to immune evasion in NSCLC lines (35). These important studies as well as the recent clinical trials with immune check point blockade have led to the initiation of a clinical trial combining PD-1 antibody, 5-azacitidine and entinostat in NSCLC patients (http://clinicaltrials.gov/ct2/show/NCT01928576?term=entinostat+pd-1&rank=1). It will be interesting to determine the importance of both changes in gene expression in the tumor cells and changes in the number and function of MDSCs in this trial. Our observations raised a number of questions. For example, what are the mechanisms underlying the selective suppression of MDSCs by epigenetic and PI3K inhibitors? Would other approaches (e.g. myelosuppressive agents) targeting immune suppressor cells synergize with immune checkpoint blockade for complete eradication of solid tumors and their metastases? Would priming with epigenetic inhibitors prior to immune checkpoint blockade work as well as concomitant administration of the two as done in the current study? Experiments addressing these questions may lead to the development of more effective therapies harnessing the power of immunity.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Materials and Methods
Reagents.
HyClone RPMI 1640 with L-Glutamine and McCoy's 5A were purchased from Invitrogen Life Technologies. HyClone Fetal Bovine Serum (FBS) was purchased from Thermo Scientific. Collagenase from *Clostridium histolyticum*, Type IV was purchased from Sigma-Aldrich. The following antibodies and reagents were used for animal experiments: mCD152 (mCTLA-4) monoclonal antibody (9H10, BioXCell), mPD-1 monoclonal antibody (RMP1-14, BioXCell), mCD25 monoclonal antibody (PC61.5.3, BioXCell), mLy6G monoclonal antibody (RB6-8C5, BioXCell), Polyclonal Hampster IgG (BioXCell), entinostat (BPS Bioscience), 5-azacytidine (Invivogen).

Cell Lines.
4T1 (CRL-2539, murine breast tumor cells) and CT26 (CRL-2638, murine colorectal adenocarcinoma) were purchased from ATCC. Both tumor cell lines were grown in McCoy's 5A supplemented with 10% Fetal Bovine Serum at 37° C., 5% CO2.

Preparation of Illumina Genomic DNA Libraries.
Genomic DNA libraries were prepared following Illumina's (Illumina) suggested protocol with the following modifications. 2-3 µg of genomic DNA were diluted with TE, to a final volume of 100 µl and sheared in a Covaris sonicator (Covaris) to an average size of 200 bp. DNA was then purified with a Nucleospin kit (Macherey-Nagel), and eluted with 50 µl of elution buffer. All reagents used for the following steps were from New England Biolabs (NEB) unless otherwise noted. 45 µl of purified DNA was then mixed with 40 µl of ddH2O, 10 µl of End Repair buffer and 5 µl of End Repair enzyme. The mixture was incubated at 20° C. for 30 min, purified by a Qiagen PCR purification kit (Qiagen) and eluted with 42 µl of elution buffer (EB) warmed to 70° C. The end repair reaction was then A-tailed using 42 µl of end-repaired DNA, 5 µl of 10×dA Tailing Reaction buffer and 5 µl of Klenow Fragment (3' to 5' exo-) and incubated at 37° C. for 30 min then purified with a MinElute PCR purification kit (Qiagen). Purified DNA was eluted with 27 µl of 65° C. EB. Adaptor ligation was performed with 25 µl of A-tailed DNA, 10 µl of PE-adaptor (Illumina), 10 µl of 5× Ligation buffer and 5 µl of Quick T4 Ligase. The ligation mixture was incubated at 20° C. for 15 min. Purification was done using by mixing 50 µl of the ligation mixture with 200 µl of NT buffer from NucleoSpin Extract II kit (Clontech) and loaded into a NucleoSpin column. The column was centrifuged at 14,000 g in a desktop centrifuge for 1 min, washed once with 600 µl of wash buffer (NT3 from Clontech), and centrifuged again for 2 min to dry completely. DNA was eluted in 50 µl elution buffer included in the kit. Purified ligated DNA was PCR amplified under the following conditions. Around 10 reactions were set up consisting of 32.5 µl of H2O, 2.5 µl (DMSO), 10 µl of 5× Phusion HF buffer, 1.0 µl of a dNTP mix containing 10 mM of each dNTP, 0.5 µl of Illumina PE minter #1, 0.5 µl of Illumina PE primer #2, 0.5 µl of Hotstart Phusion polymerase, and 5 µl of ligated DNA. The PCR program used was: 98° C. 1 minute; 10 to 16 cycles of 98° C. for 20 seconds, 65° C. for 30 seconds, 72° C. for 30 seconds; and 72° C. for 5 min. The reactions were then pooled and purified with a 12 mixture of PCR product and NT buffer from a NucleoSpin Extract II kit and purified via the protocol contained within the kit. Library DNA was eluted with 70° C. elution the DNA concentration was estimated by absorption at 260 nm with a nanodrop and then the samples proceeded to Sureselect exome isolation.

Exome Capture.
The mouse exome was captured following a protocol from Agilent's SureSelect Paired-End Mouse Exome Kit (Agilent) with the following modifications. (1) A hybridization mixture was prepared containing 25 µl of SureSelect Hyb #1, 1 µl of SureSelect Hyb #2, 10 µl of SureSelect Hyb #3, and 13 µl of SureSelect Hyb #4. (2) 3.4 µl (0.5 µg) of the PE-library DNA described above, 2.5 µl of SureSelect Block #1, 2.5 µl of SureSelect Block #2 and 0.6 µl of Block #3; was loaded into one well in a 384-well Diamond PCR plate (cat # AB-1111, Thermo-Scientific), sealed with 2 layers of microAmp clear adhesive film (cat #4306311; ABI) and placed in GeneAmp PCR system 9700 thermocycler (Life Sciences Inc.) for 5 min at 95° C., then held at 65° C. (with the heated lid on). (3) 25 µl of hybridization buffer from step (1) was heated for at least 5 mm at 65° C. in another sealed plate with heated lid on. (4) 5 µl of SureSelect Oligo Capture Library, 1 µl of nuclease-free water, and 1 µl of diluted RNase Block (A 1:1 RNase Block, nuclease-free water mix) were mixed and heated at 65° C. for 2 min in another sealed 384-well plate. (5) While keeping all reactions at 65° C., 13 µl of Hybridization Buffer from Step (3) was quickly added to the 7 µl of the SureSelect Capture Library Mix from Step (4) and then the entire contents (9 µl) of the library from Step (2). The mixture was pipetted up and down 10 times. (6) The 384-well plate was sealed tightly and the hybridization mixture was incubated for 24 hours at 65° C. with a heated lid. After hybridization, five steps were performed to recover and amplify the captured DNA library: (1) 50 µl of Dynal MyOne Streptavidin C1 magnetic beads (Cat #650.02, Invitrogen Dynal) was placed in a 1.5 ml microfuge tube and vigorously resuspended on a vortex mixer. Beads were washed three times by adding 200 µl of SureSelect Binding buffer, mixing on a vortexer for five seconds and then placing the tubes in a Dynal magnetic separator prior to removing the supernatant after. After the third wash, beads were resuspended in 200 µl of SureSelect Binding buffer. (2) To bind captured DNA, the entire hybridization mixture described above (29 µl) was transferred directly from the thermocycler to the bead solution and immediately inverted a 4 times to mix; the hybridization mix/bead solution was then incubated in an Eppendorf thermomixer at 850 rpm for 30 min at room temperature. (3) To wash the beads, the supernatant was removed from beads after applying a Dynal magnetic separator and the beads were resuspended in 500 µl SureSelect Wash Buffer #1 by mixing on vortex mixer for 4 seconds and incubated for 15 min at room temperature. Wash Buffer #1 was then removed from beads after magnetic separation. The beads were further washed three times, each with 500 µl pre-warmed SureSelect Wash Buffer #2 after incubation at 65° C. for 10 min. After the final wash, SureSelect Wash Buffer #2 was completely removed. (4) To elute captured DNA, the beads were suspended in 50 µl SureSelect Elution Buffer, vortex-mixed and incubated for 10 min at room temperature. The supernatant was removed after magnetic separation, collected in a new 1.5 ml microcentrifuge tube, and mixed with 50 µl of SureSelect Neutralization Buffer. DNA was purified with a Qiagen MinElute column and eluted in 17 µl of 65° C. buffer EB to obtain 15 µl of captured DNA library. (5) The captured DNA library was amplified in the following way: Approximately 15 PCR reactions each containing 9.5 µl of $H_2O$, 3 µl of 5× Phusion HF buffer, 0.3 µl of 10 mM dNTP, 0.75 µl of DMSO, 0.15 µl of Illumina PE primer #1, 0.15 µl of Illumina PE primer #2, 0.15 µl of Hotstart Phusion polymerase, and 1 µl of captured exome library were set up. The PCR program used was: 98° C. for 30 seconds; 14 cycles of 98° C. for 10 seconds, 65° C. for 30 seconds, 72° C. for 30 seconds; and 72° C. for 5 min. To purify PCR products, 225 µl of PCR mixture (from 15 PCR reactions) was mixed with 450 µl of NT buffer from NucleoSpin Extract II kit and purified as described above. The final library DNA was eluted with 30 µl of 65° C. elution buffer and DNA concentration was estimated by $OD_{260}$ measurement.

Preparation of cDNA for Sequencing Analysis.

mRNA was prepared from 5-10 µg total RNA using two rounds of poly-A selection using Dynal oligo-dT magnetic beads following the manufacturers protocol (Life Technologies) and eluted the second time with 13 µl of elution buffer. Double-stranded (ds) cDNA was prepared using the SuperScript ds-cDNA kit (Invitrogen) with the following modifications. 12 µl of the isolated mRNA was added to 2 µl of 50 ng/µl random hexamers and incubated at 70° C. for 10 minutes then placed on ice. 4.4 µl of 5× First Strand Buffer, 2.2 µl of 0.1 M DTT and 1.1 µl of a 10 mM dNTP mixture were added to the tube and incubated at 45° C. for 2 minutes upon which 1.5 µl of SSII enzyme was added and the entire mixture incubated for an additional 1 hour and then placed on ice. Second Strand cDNA was made by adding to the first strand reaction 90 µl of $ddH_2O$, 30 µl of 5× Second Strand Buffer, 3 µl of 10 mM dNTPs, 4 µl of DNA Pol I, 1 µl of RNaseH and 1 µl of E. coli DNA ligase. The mixture was then incubated at 16° C. for 2 hours upon which 2 µl of T4 ligase was added and incubated for an additional 5 minutes. The resulting cDNA was then purified using a Qiagen PCR purification kit following the manufacturer's instructions and eluted twice with 50 µl of 70° C. elution buffer each time. The 100 µl of cDNA was used for the construction of illumina libraries following the genomic DNA library protocol with the cDNA in place of genomic DNA.

Somatic Mutation Identification.

Libraries were sequenced on Illumina GAIIx or HiSeq Genome Analyzer. Sequencing reads were analyzed and aligned to mouse genome mm9 with CASAVA (Illumina) A mismatched base was identified as a mutation only when (i) it was identified by four or more distinct pairs containing at least 2 reads in the forward and 2 in the reverse orientation; (h) the number of distinct tags containing a particular mismatched base was at least 30% of the total distinct tags.

Identification of Putative Expressed H2-(d) Epitopes.

Identified somatic mutations were cross-referenced against the RNAseq data to determine which mutations were expressed. The amino acid change corresponding to the positive mutations were then used for mutant epitope identification by isolating 8 amino acids up- and down-stream of the mutant residue. This seventeen amino acid sequence was than processed using the netMHC epitope identification algorithm (netMHC v3.4) for potential 9 amino acid binders to H2-k(d), H2-L(d) and H2-D(d). The cutoff used was 500 nM affinity or higher which corresponds to moderate to high affinity binders. Genes were determined to be expressed if the normalized counts (normalized to length per million reads) of RNAseq data were greater than 0.5.

Animal Models.

Animal research was approved and overseen by Johns Hopkins University Institutional Animal Care and Use Committee. Six to eight weeks old female BALB/C mice (Harlan Laboratories) were used for all animal experiments. $5\times10^6$ 4 T1 tumor cells or $5\times10^6$ CT26 tumor cells were inoculated subcutaneously into the right flank of each mouse. Tumors were allowed to grow for 11 days prior to randomization and treatment. CT26 bearing mice were given 10 mg/kg of anti-PD-1 and/or anti-CTLA-4 antibodies intraperitoneally on day 11, 13, 15, 17, 20, 23 and 26 post-tumor implantations and 4T1 bearing mice were given 10 mg/kg anti-PD-1 and/or anti-CTLA-4 antibodies intraperitoneally on day 11, 13, 15, and 17 post-tumor implantations. 4T1 tumor bearing mice were given a single dose of 10 mg/kg anti-CD25 antibody or 10 mg/kg anti-Ly6G antibody intraperitoneally on day 12 post-tumor implantation for cell depletion studies. All antibodies were diluted to appropriate concentrations in 100 µl sterile PBS, pH 7.4 (Invitrogen Life Technologies). Entinostat and 5-azacytidine treatments were started on day 12 post-tumor implantation at a dose of 20 mg/kg and 0.8 mg/kg, respectively. 4T1 bearing mice were injected intraperitoneally on day 12, 14, 16, and 18. J32 was given at 22 mg/kg by intraperitoneal injections on day 12, 14, 16, and 18 of 4T1 tumor implantation. Tumors were measured for 30 days from the start of the treatment at indicated intervals in the results section. Tumor volume was calculated as length×width×0.5.

Metastasis Analysis.

On day 46 post-tumor implantations, 4T1 tumor bearing mice were euthanized according to the IACUC guidelines. Lungs, livers and spleens were harvested and fixed in 10% Neutral Buffered Formalin Solution (Sigma-Aldrich) and metastatic nodules were counted from at least three mice per group.

Flow Cytometry.

The following antibodies and reagents were used for flow cytometry: CD16/32 (BD Biosciences), CD3e Alexa Fluor 488 (14-C11; BD Biosciences), CD4 Brilliant Violet 421 (GK1.5, BD Biosciences), CD8a PerCP-Cy5.5 (53-6.7, BD Biosciences), CD25 PE (PC61, BD Biosciences), Foxp3 Alexa Fluor 647 (MF23, BD Biosciences), CD11b Alexa Fluor 700 (M1/70, BD Biosciences), I-A/I-E Alexa Fluor 488 (M5/114.15.2, BD Biosciences), Ly-6C PerCP-Cy5.5 (AL-21, BD Biosciences), CD11c PE (HL3, BD Biosciences), F4/80 APC (BM8, Biolegend), Ly-6G Pacific Blue (1A8, Biolegend), CD45 Pacific Orange (30-F11, Invitrogen Life Technologies), and Live/Dead Fixable Near IR Dead Cell Stain (Invitrogen Life Technologies). Flow cytometry was performed with LSR II (BD Biosciences) and the data was analyzed with FACS Diva software (BD Biosciences). To assess the level of circulating G-MDSC population, blood samples were collected from the mice 7 days after the initiation of the anti-PD-1/anti-CTLA-4 antibody treatments with or without 5-AZA/Entinostat. 150 µl of blood was collected into $K_2$EDTA BD Microtainer (BD Biosciences) from either right or left facial vein. RBCs from anti-coagulated blood samples were immediately lysed using 2 ml of 1×BD FACS Lyse (BD Biosciences) for 3 minutes and the samples were washed twice in ice-cold BD FACS Buffer (BD Biosciences). After 5-minute incubation with Live/Dead Fixable Near IR Dead Cell Stain and two washes with ice-cold BD FACS Buffer, the samples were stained with appropriate antibodies. For analysis, we used previously established phenotypic criteria of these cells as $CD45^+CD11b^+Ly6G^+Ly6C^{lo}F4/80^-MHCII^-$ cells and total CD45 positive cells were used as a common denominator. To assess the level of intratumoral $CD8^+$ and regulatory T cell populations, lymphocytes were first purified from tumor samples excised from mice 7 days after the initiation of the anti-PD-1/anti-CTLA-4 antibody treatments with or without 5-AZA/Entinostat. Briefly, primary tumor tissues were harvested, weighed, and minced to fine fragments. Collagenase IV (Sigma-Aldrich) at 1 mg/ml in HBSS (Invitrogen Life Technologies) was added to each sample at a ratio of 1 ml per 200 mg of tumor tissue. Samples were incubated on an end-over-end shaker for 30 minutes at 37° C. The resulting tissue homogenates were 0.4 µm filtered, washed three times in ice-cold BD FACS Buffer (BD Biosciences), and $5×10^6$ cells per sample were used for antibody labelling. $CD8^+$ T cell level was assessed using previously established phenotypic criteria of $CD45^+CD3^+CD8^+$ and total $CD45^+CD3^+$ cells was used as a common denominator. Treg cell level was assessed using previously established phenotypic criteria of $CD45^+CD3^+CD4^+CD25^+FoxP3^+$ and total $CD45^+CD3^+CD4^+$ cells were used as a common denominator.

Cell Isolation.

MDSCs from 4T1 tumor-bearing animals were isolated from spleens using Myeloid-Derived Suppressor Cell Isolation Kit, mouse (Miltenyi Biotec) and BD FACS Aria III cell sorter (BD Biosciences). $CD8^+$ cells were isolated from spleens of 4T1-bearing animals treated with anti-PD-1 and anti-CTLA-4 antibodies using $CD8a^+$ T Cell Isolation Kit II, mouse (Miltenyi Biotec) and BD FACS Aria III cell sorter (BD Biosciences). MDSC, Tregs, and $CD8^+$ T cells were isolated and cultured by following the manufacturer's protocols and published protocols (38, 39). The purity of G-MDSCs ($CD11b^+Ly6G^+Ly6C^{lo}F4/80^-MHC-II^-$) and $CD8^+$ ($CD3^+CD8^+$) populations were greater than 95% as determined by flow cytometry, and the viability was greater than 95% for these populations as determined by trypan blue staining.

In Vitro Survival Assay.

MDSCs and $CD8^+$ T cells were plated on 96-well plate at $2×10^6$ cells/ml in RPMI1640 medium supplemented with 10% FBS. $CD8^+$ T cell cultures were supplemented with recombinant interleukin-2 (Invitrogen Life Technologies) at 2000 U/ml. 4T1 cells in McCoy 5A supplemented with 10% FBS were plated on 96-well plate and cultured until they reached >70% confluency. Cells were cultured with entinostat, 5-azacytidine, or J32 at concentrations ranging from 0 µM to 50 µM for 24 hours at 37° C., 5% $CO_2$. The proportion of viable cells was assessed by incubating the cells with 10% (v/v) Cell Proliferation Reagent WST-1 (Roche Applied Science) for 3 hours at 37° C. and measuring $OD_{450}$ absorbance of the resulting formazan products.

IFN-γ Assay.

Freshly isolated MDSCs and $CD8^+$ T cells from 4T1 tumor-bearing animals were cultured at MDSC to $CD8^+$ T cell ratios of 5:1, 2:1, 1:1, 1:2, and 1:5 in presence of recombinant IL-2 (Invitrogen Life Technologies) at 2000 U/mL and CD3/CD28 antibody coated beads (Miltenyi). MDSC and $CD8^+$ T cells were cultured at 1:1 ratio with entinostat at concentrations ranging from 0 µM to 0.25 µM. Cell-free supernatants were collected after 24-hour incubation at 37° C. and IFN-γ levels were assayed using Mouse IFN-γ DuoSet Elisa Development Kit (R&D Systems) according to the manufacturer's instruction.

MDSC Depletion and Adoptive Transfer.

For in-vivo depletion of MDSC, 4T1 tumor-bearing mice were treated with a single bolus of mLy6G monoclonal antibody at 10 mg/kg administered intraperitoneally on day 11 post-tumor implantation. For adoptive transfer of MDSC, spleens from 4T1-bearing mice were collected and MDSCs were purified with Myeloid-Derived Suppressor Cell Isolation Kit, mouse (Miltenyi Biotec). After two sequential column purifications, cells were washed twice in ice-cold 1×PBS (Invitrogen Life Technologies) and cell concentration was adjusted to $1×10^8$ cells/ml. Cell viability was greater than 95% as verified with trypan blue staining and cell purity was greater than 90% as determined by flow cytometry. Immediately following the isolation, 100 µl of MDSCs at $1×10^8$ cell/ml were administered via tail vein injection on day 11, 13, and 15 post 4T1 tumor implantation.

Immunofluorescence.

Mice were euthanized according to the JHU IUCAC guidelines and primary tumors from 4T1 tumor-bearing mice were excised using sterile disposable surgical scalpels (Bard-Parker). Excised tissues were placed in base molds filled with Tissue-Tek CRYO-OCT (Andwin Scientific) and stored at −80° C. until use. Frozen tissues were sectioned using Leica CM3050 S Cryostat (Leica Biosystems) and tissues were fixed with 4% Paraformaldehyde (Alfa Aesar), 0.3% Triton X-100 (Sigma-Aldrich) in 1×PBS (Invitrogen Life Technologies) for 10 minutes. Slides were washed three times with 0.05% Tween-20 (Sigma-Aldrich) in 1×PBS followed by three 5-minute washes with 0.05% Tween-20 in 1×PBS. Tissues were blocked with 3% BSA (Sigma-Aldrich), 0.05% Tween-20 in 1×PBS for 30 minutes, followed by an additional 30-minute block with 10% normal goat serum (Invitrogen Life Technologies). Blocked tissues were incubated overnight in anti-CD8 (YTS 169.4, Abcam) or anti-Ly6G (RB6-8C5, Abcam) at concentrations 1:50, 1:100, and 1:200 at 4° C. Following the overnight staining with primary antibodies, the slides were washed three times with 0.05% Tween-20 in 1×PBS and incubated with 1:500 goat anti-rat AF488 (Invitrogen Life Technologies) or goat anti-rat AF594 (Invitrogen Life Technologies) secondary antibodies for 1 hour at 20° C. Slides were washed five times with 0.05% Tween-20 in 1×PBS, one drop of Gold/DAPI (Invitrogen Life Technologies) was added to the tissue samples prior to placing a cover slip, and the slides were stored at 4° C. in dark. For imaging, Nikon C1 Laser Scanning Confocal System, which includes ECLIPSE TE2000-E microscope and EZ-LIMO for Nikon C1 Confocal v.2.30 was used.

Reverse-Transcription PCR (RT-PCR).

$5 \times 10^6$ CT26 or 4T1 cells were resuspended in 0.75 ml Trizol LS Reagent (Invitrogen Life Technologies) and 0.25 ml chloroform (Sigma-Aldrich). Samples were vortexed for 15 seconds and incubated for 10 minutes at 20° C. After a 15-minute 12000 g centrifugation at 4° C., upper aqueous phase was collected and 0.5 ml of 100% isopropanol (Sigma-Aldrich) was added. Samples were centrifuged at 12000 g for 10 minutes at 4° C. after 10 minute incubation at 20° C. The resulting pellets were air dried for less than 10 minutes and were resuspended with RNAse-free water (Invitrogen Life Technologies) for a final concentration of 500 ng/μl. PCR was performed using SuperScript III One-Step RT-PCR System with Platinum Taq DNA Polymerase (Invitrogen Life Technologies). Annealing temperature was set at 55° C. for H-2D(d), β2m and TAP1, and set at 60° C. for β-actin. Samples were analyzed on 1% agarose gel. The following minters were used for RT-PCR: H-2D(d) Forward 5'-agggcaatgagcagagtttc-3' (SEQ ID NO: 1), H-2D(d) Reverse 5'-CCACGTTTTCAGGTCTTCGT-3' (SEQ ID NO: 2), β2m Forward 5'-ATTCACCCCCACTGAGACTG-3' (SEQ ID NO: 3), β2m Reverse 5'-GCTATTTCTTTCTGCTGTGCAT-3' (SEQ ID NO: 4), TAP1 Forward 5'-GAGACATGCTGTGTCGGATG-3' (SEQ ID NO: 5), TAP1 Reverse 5'-TGGTGAGAATGGACATGAGC-3' (SEQ ID NO: 6), β-actin Forward 5'-TTCTTTGCAGCTCCTTCGTTGCCG-3' (SEQ ID NO: 7), β-actin Reverse 5'-TGGATGGCTACGTA-CATGGCTGGG-3' (SEQ ID NO: 8).

Statistics.

All statistics analyses were performed with Prism 5.0 (GraphPad Software, Inc). Primary tumor growth curves were first analyzed with two-way ANOVA and individual groups were compared with two tailed Wilcoxon rank-sum test. Kaplan-Meier survival curves were analyzed with log-rank test. Statistical significance of metastatic lesions, flow cytometric analyses, and in-vitro assays were assessed with two tailed Wilcoxon rank-sum test.

Example 2

Genetic Analysis.

We first sequenced the exomes (24,306 genes) of both CT26 and 4T1 cells. Eight and 3.5 gigabases of generated sequence were mapped to the genome for CT26 and 4T1, respectively. 83.5% (CT26) and 72.3% (4T1) of bases in the targeted regions were covered by at least 10 unique reads in tumor DNA. Sequencing of the exomes revealed 683 and 47 somatic mutations in CT26 and 4T1, respectively (Dataset S1).

It has been shown that ~10% of the mutant amino acids created by somatic mutations in human colorectal and breast cancers give rise to epitopes that are predicted to be recognized by the patient's MHC-I alleles (17). To determine whether this was true for the murine colorectal (CT26) and breast (4T1) tumors, we mapped the somatically mutated epitopes to BALB/c MHC-I using established algorithms. As such predictions are meaningful only if the mutant genes are expressed, we determined the transcriptomes of the two cell lines using RNA-Seq. Three hundred and fourteen of the 683 mutations detected in CT26 occurred in expressed genes, with 28 mutated epitopes predicted to bind with at least moderate affinity to H2-(d) MHC-I alleles found in BALB/c mice (Dataset S1 and Table 1). The 4T1 cells harbored 27 mutations in expressed genes with only one predicted to bind to H2-(d) MHC-I alleles. These data are consistent with the suggestion that CT26 is more immunogenic than 4T1 because the former has more mutant epitopes. It is also consistent with the observation that human tumors associated with environmental mutagens (such as UV light and cigarette smoke) have more mutations than other tumors (18).

TABLE 1

Mutant MHC-I Epitopes predicted from genome and transcriptome analyses

| | Name | Epitope | Affinity (nM) | H-2 Allele |
|---|---|---|---|---|
| CT26 Tumor Cell | | | | |
| SEQ ID NO. 9 | AE2f8 | SGPSYATYL | 362 | H-2Dd |
| SEQ ID NO. 10 | Haus6 | SYETLKKSL | 21 | H-2Kd |
| SEQ ID NO. 11 | Slc20a1 | SYTSYIMAI | 28 | H-2Kd |
| SEQ ID NO. 12 | Sel11 | RYWTGIGVL | 46 | H-2Kd |
| SEQ ID NO. 13 | Glud1 | AYVNAIEKI | 49 | H-2Kd |
| SEQ ID NO. 14 | Noc31 | SYIKKLKEL | 58 | H-2Kd |
| SEQ ID NO. 15 | Em15 | HYLNDGDAI | 66 | H-2Kd |
| SEQ ID NO. 16 | Gnas | KVLAGKSTI | 74 | H-2Kd |
| SEQ ID NO. 17 | Mtor | HHTMMVQAI | 126 | H-2Kd |
| SEQ ID NO. 18 | Map3k5 | AYALNRRNL | 131 | H-2Kd |
| SEQ ID NO. 19 | Slc20a1 | SYIMAICGM | 146 | H-2Kd |
| SEQ ID NO. 20 | Dhx35 | YYMRDVIAI | 211 | H-2Kd |
| SEQ ID NO. 21 | Pigo | LFLKSPTAL | 265 | H-2Kd |
| SEQ ID NO. 22 | Ptpn13 | PYFRLEHYL | 311 | H-2Kd |
| SEQ ID NO. 23 | Qsox1 | SYLRRLPGL | 316 | H-2Kd |
| SEQ ID NO. 24 | Tars12 | TYWKGNPEM | 332 | H-2Kd |
| SEQ ID NO. 25 | Anks6 | GYEAVVRLL | 338 | H-2Kd |
| SEQ ID NO. 26 | Slc41a2 | PYLTALDDL | 365 | H-2Kd |
| SEQ ID NO. 27 | Pdgfra | LFVTVLEVI | 404 | H-2Kd |
| SEQ ID NO. 28 | Rwdd2b | VYFTINVNL | 432 | H-2Kd |
| SEQ ID NO. 29 | Vps26b | SYTEQNVKL | 460 | H-2Kd |
| SEQ ID NO. 30 | Qsox1 | FYTSYLRRL | 496 | H-2Kd |
| SEQ ID NO. 31 | Phf3 | FPPQNMFEF | 5 | H-2Ld |
| SEQ ID NO. 32 | Trim26 | SPEAQLFAV | 112 | H-2Ld |
| SEQ ID NO. 33 | Zfp449 | EPQIAMDDM | 115 | H-2Ld |
| SEQ ID NO. 34 | Csnk2b | IPDEAMVKL | 184 | H-2Ld |
| SEQ ID NO. 35 | Zeb1 | EPQVEPLDF | 272 | H-2Ld |
| SEQ ID NO. 36 | Ttc15 | DPFATPLSM | 485 | H-2Ld |
| 4T1 Tumor Cell | | | | |
| SEQ ID NO. 37 | Qars | FPPDAINNF | 27 | H-2Dd |

Example 3

Effects of Immune Checkpoint Blockade.

Figures 1A, 1B, 1C, 1D, 1E, 1F, 1G:
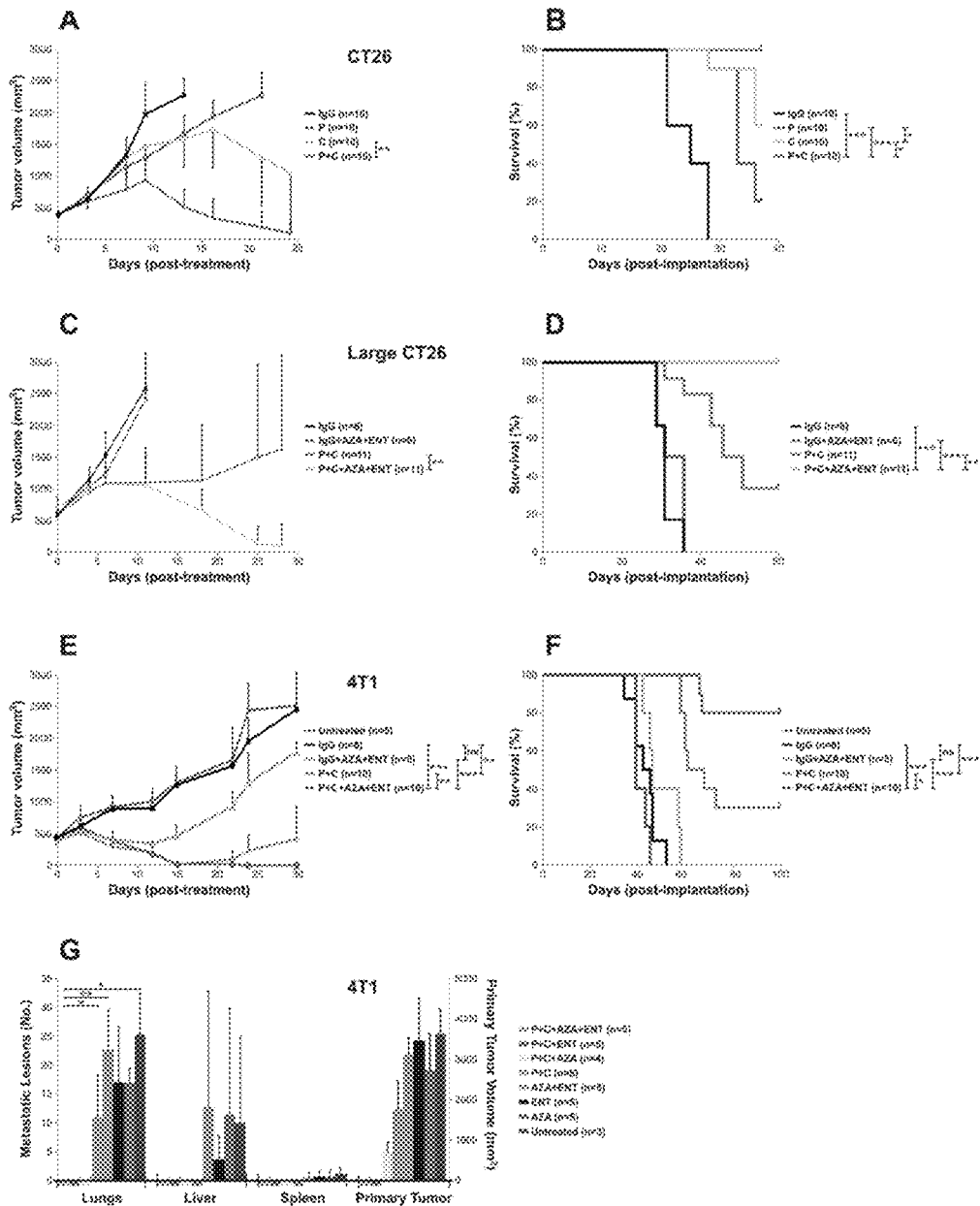
FIGS. 1A to 1G. Therapeutic response of tumor-bearing mice. BALB/c mice bearing different tumors were treated with various therapeutic modalities as indicated. IgG, IgG control; P, anti-PD-1 antibody; C, anti-CTLA-4 antibody, AZA, 5-azacytidine; ENT, entinostat. Tumor volumes (FIG. 1A, FIG. 1C, and FIG. 1E) and animal survival (FIG. 1B, FIG. 1D, and FIG. 1F) were recorded.

We then tested the effects of immune checkpoint blocking antibodies on tumors derived from these cells in mice. BALB/c mice bearing subcutaneous CT26 tumors of moderate sizes (~400 mm³) were used for the initial experiments. While repeated treatment with anti-CTLA-4 or anti-PD-1 antibodies as single agents retarded tumor growth, tumor eradication was not observed (FIGS. 1A and B). Combination therapy with both antibodies resulted in eradication of tumors in vast majority of the mice. Conversely, tumors larger than 600 mm$^3$ did not respond to the combined anti-PD-1/anti-CTLA4 treatment as well (FIG. 1C), with only 4 out of 11 animals showing long-term survival (FIG. 1D).

Next, BALB/c mice with well-established 4T1 tumors (~400 min) were evaluated; these tumors spontaneously metastasize to the lungs and other organs. The 4T1 tumor model is highly recalcitrant to most therapeutic agents, including immunotherapy (16). The animals generally succumb to metastatic disease, even when the primary tumor is surgically removed (19). Small number of the primary tumors showed durable response to antibody treatment. Similar to the mice with large CT26 tumors, only 3 out of 10 animals showed complete regression of their primary tumors when treated with both anti-PD-1 and anti-CTLA-4 antibodies, and these were the only long-term survivors (FIGS. 1 E and F).

Example 4

Epigenetic Modulation.

We hypothesized that the tumors in the animals that had not been cured might have down-regulated the expression of MHC-I-related genes through epigenetic silencing in tumor cells. Indeed, this hypothesis forms the basis for therapies involving epigenetic modulation (20), using inhibitors of either DNA methyltransferase or histone deacetylase (HDAC). To evaluate this possibility, we treated animals bearing large CT26 tumors (>600 mm$^3$) as described above with anti-PD-1/anti-CTLA-4 antibodies as well as 5-azacytidine (AZA, a DNA methyltransferase inhibitor) and entinostat (ENT, a class I HDAC inhibitor). The tumors responded to this regimen remarkably well, with eradication of primary tumors in 10 out of 11 mice and 100% survival 60 days after tumor implantation (FIG. 1D). Similarly, in response to the anti-PD-1/anti-CTLA-4 plus AZA/ENT treatment, mice with 4T1 tumors (~400 mm$^3$) showed complete regression of all primary tumors three weeks after treatment initiation and 80% survival 100 days after tumor implantation (FIGS. 1 E and F). Temporary self-limiting toxicity, as indicated by body weight changes, was observed when entinostat was used (FIG. 37). However, the addition of anti-PD-1/anti-CTLA-4 antibodies did not add to the toxicity.

In parallel experiments, we treated 4T1 tumor-bearing mice as described above but sacrificed them six weeks after tumor implantation. We then examined their primary tumors as well as lungs and other organs for metastasis. The primary tumors were eradicated in all five mice treated with anti-PD-1/anti-CTLA-4 antibodies plus AZA/entinostat and none of them showed any metastases (FIG. 1G and Table 2). In contrast, all five mice with anti-PD-1/anti-CTLA-4 treatment alone still bad large primary tumors and an average of 11 lung metastases. We also treated the tumor-bearing mice with anti-PD-1/anti-CTLA-4 antibodies plus either entinostat or AZA. No primary tumors or metastases were found in any of the mice treated with anti-PD-1/anti-CTLA-4 antibodies plus entinostat, suggesting that when combined with PD-1/CTLA-4 double blockade, class I HDAC inhibitors alone (without DNA methylation inhibitors) were sufficient to eradicate both primary tumors and metastasis (FIG. 1G and Table 2). In the mice treated with anti-PD-1/anti-CTLA-4 antibodies plus AZA, the primary tumors were not eradicated, though no metastases were observed. Without PD-1/CTLA-4 inhibition, entinostat, AZA, alone or in combination, were unable to eradicate either primary tumor or metastasis (FIG. 1G and Table 2). When PD-1/CTLA-4 inhibition was not applied, metastatic lesions were observed in multiple organs in addition to those in the lungs.

TABLE 2

4T1 Primary Tumors and Metastatic Lesions

| Treatment Group | Mouse No | Primary Tumor Vol (mm$^3$) | Lung Mets | Liver Mets | Spleen Mets |
| --- | --- | --- | --- | --- | --- |
| P + C AZA + ENT | 1 | 0 | 0 | 0 | 0 |
| | 2 | 0 | 0 | 0 | 0 |
| | 3 | 0 | 0 | 0 | 0 |
| | 4 | 0 | 0 | 0 | 0 |
| | 5 | 0 | 0 | 0 | 0 |
| | AVERAGE | 0 | 0 | 0 | 0 |
| | STDEV | 0 | 0 | 0 | 0 |
| P + C ENT | 1 | 0 | 0 | 0 | 0 |
| | 2 | 0 | 0 | 0 | 0 |
| | 3 | 0 | 0 | 0 | 0 |
| | 4 | 0 | 0 | 0 | 0 |
| | 5 | 0 | 0 | 0 | 0 |
| | AVERAGE | 0 | 0 | 0 | 0 |
| | STDEV | 0 | 0 | 0 | 0 |
| P + C AZA | 1 | 435 | 0 | 0 | 0 |
| | 2 | 595 | 0 | 0 | 0 |
| | 3 | 1069 | 0 | 0 | 0 |
| | 4 | 754 | 0 | 0 | 0 |
| | AVERAGE | 713 | 0 | 0 | 0 |
| | STDEV | 271 | 0 | 0 | 0 |
| P + C | 1 | 2221 | 12 | 0 | 0 |
| | 2 | 1768 | 14 | 0 | 0 |
| | 3 | 2456 | 21 | 0 | 0 |
| | 4 | 577 | 0 | 0 | 0 |
| | 5 | 1874 | 9 | 0 | 0 |
| | AVERAGE | 1779 | 11 | 0 | 0 |
| | STDEV | 726 | 8 | 0 | 0 |
| AZA + ENT | 1 | 2891 | 34 | 10 | 0 |
| | 2 | 2855 | 14 | 0 | 0 |
| | 3 | 3613 | 22 | 49 | 2 |
| | 4 | 2726 | 25 | 0 | 0 |
| | 5 | 3597 | 22 | 7 | 1 |
| | AVERAGE | 3137 | 23 | 13 | 1 |
| | STDEV | 432 | 7 | 20 | 1 |
| ENT | 1 | 3005 | 25 | 10 | 1 |
| | 2 | 5038 | 20 | 3 | 0 |
| | 3 | 2275 | 0 | 0 | 0 |
| | 4 | 3063 | 22 | 6 | 3 |
| | 5 | 4032 | 20 | 0 | 0 |
| | AVERAGE | 3483 | 17 | 4 | 1 |
| | STDEV | 1070 | 10 | 4 | 1 |
| AZA | 1 | 2345 | 20 | 0 | 0 |
| | 2 | 2454 | 16 | 43 | 3 |
| | 3 | 2477 | 20 | 0 | 1 |
| | 4 | 4358 | 17 | 16 | 0 |
| | 5 | 2117 | 14 | 0 | 0 |
| | AVERAGE | 2750 | 17 | 12 | 1 |
| | STDEV | 910 | 3 | 19 | 1 |
| Untreated | 1 | 4359 | 32 | 3 | 2 |
| | 2 | 3432 | 28 | 0 | 2 |
| | 3 | 3185 | 18 | 28 | 0 |
| | AVERAGE | 3659 | 26 | 10 | 1 |
| | STDEV | 619 | 7 | 15 | 1 |

Example 5

Mechanistic Studies.

As noted above, we expected that the epigenetic modulators were increasing the expression of MHC-I-related genes, thereby making the cancer cells more susceptible to killing by T cells. To test this expectation, we analyzed the expression of genes involved in MHC-I presentation by reverse transcription-polymerase chain reaction (RT-PCR)

in CT26 and 4T1 cells treated with AZA, entinostat, or the combination of the two. Expression of the MHC-I, β-2 microglobulin (B2M), and transporter associated with antigen processing 1 (TAP1) genes were detected in both tumor cell lines in the absence of treatment. However, exposure to epigenetic modulators did not significantly increase the expression (FIG. S2).

We then determined whether the epigenetic modulators affected T cell accumulation within the tumors. As assessed by flow cytometry, tumor-infiltrating $CD8^+$ T cells increased by approximately four-fold after PD-1/CTLA-4 inhibition (FIGS. 2 A and B). The addition of AZA and entinostat did not increase tumor-infiltrating $CD8^+$ T cells further. However, inclusion of AZA and entinostat in the treatment regimen resulted in a significant decrease in tumor-infiltrating $FoxP3^+$ Tregs compared to either untreated tumors or tumors treated with anti-PD-1/CTLA-4 antibodies (FIGS. 2 C and D).

Figures 2A, 2B, 2C, 2D, 2E, 2F, 2G, 2H:
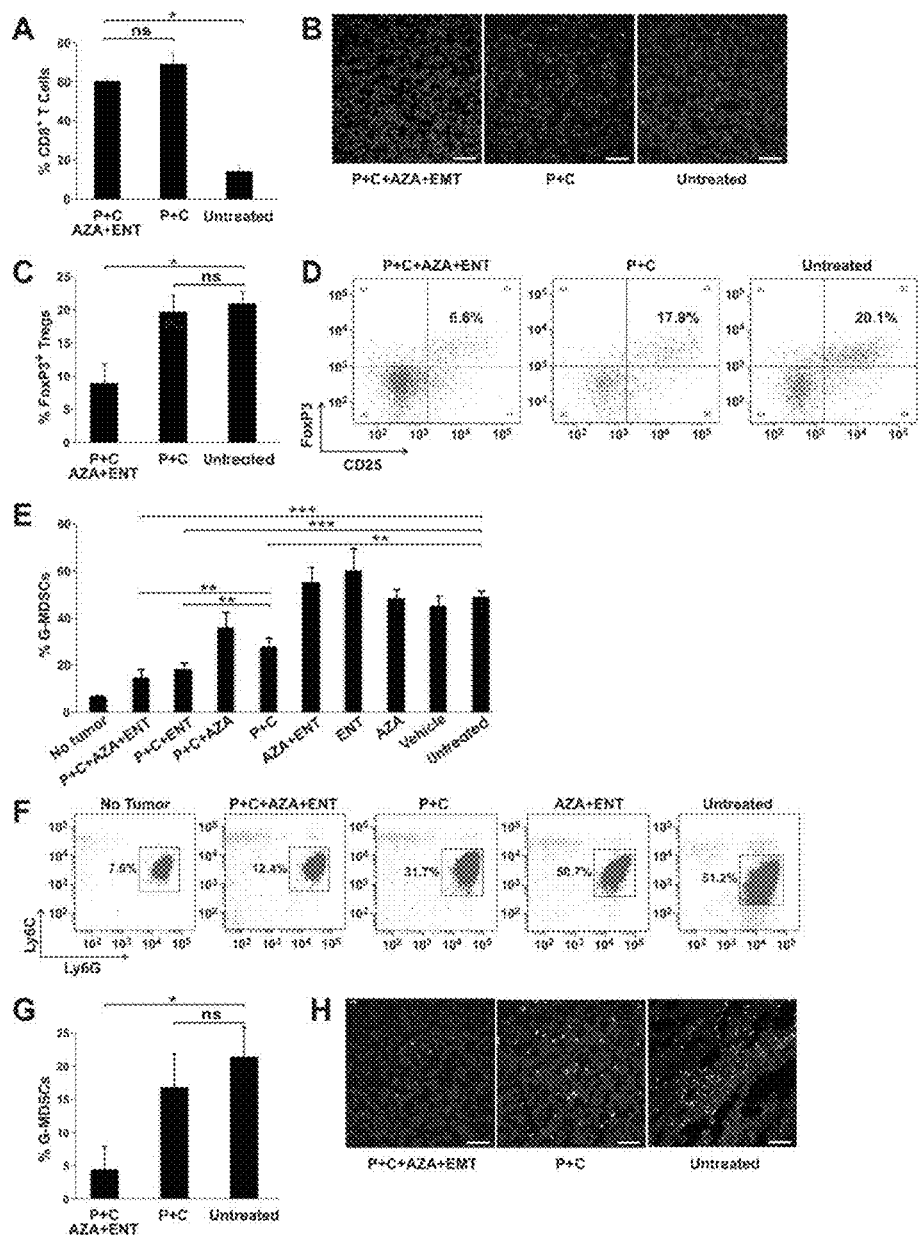
FIGS. 2A-2H. Response of immune cells following immune checkpoint blockade and epigenetic modulation. BALB/c mice bearing metastatic 4T1 tumors were treated with indicated therapeutic modalities, followed by FACS and immunohistofluorescent analyses to assess tumor-infiltrating and circulating immune cells. Means and standard deviations are shown, with P-values indicated.

We next analyzed MDSCs by flow cytometry, as these myeloid-derived immature cells are often elevated in tumor-bearing hosts and have potent immunosuppressive activities (21, 22). We found that 4T1 tumor-bearing mice had a five to seven-fold increase in circulating Granulocytic MDSCs (G-MDSCs, defined as $CD11b^+Ly6G^+Ly6C^{lo}MHC-II^-$) compared to non-tumor-bearing animals (FIG. 2E, FIGS. S3 A and B). Large numbers of G-MDSCs were also observed in the spleen and tumor (FIG. S3B). Addition of entinostat or AZA/entinostat to PD-1/CTLA-4 inhibition resulted in a striking reduction in the number of circulating G-MDSCs, bringing them down to a level similar to that observed in non-tumor-bearing mice (FIGS. 2 E and F). Interestingly, the epigenetic modulators alone or AZA plus anti-PD-1/anti-CTLA-4 antibodies failed to abate the G-MDSCs. The epigenetic modulators substantially reduced the number of tumor-infiltrating G-MDSCs as well when combined with immune checkpoint blockade (FIG. 2 G and H).

These data are consistent with the hypothesis that immune checkpoint blockade leads to expansion of cytotoxic effector T cells (Tells), but the Tells are not fully functional unless immune suppressor cells are reduced by treatment with epigenetic modulators. To further test this hypothesis, we used neutralizing antibodies against CD25 or Ly6G to deplete Tregs or G-MDSCs, respectively, in mice bearing 4T1 tumors (23-25). We found that anti-Ly6G, when used in combination with anti-PD-1/anti-CTLA-4 antibodies, were as effective as the epigenetic modulators (FIG. 3A). Flow cytometry showed a substantial reduction in G-MDSC levels after anti-Ly6G treatment (FIG. 3B). In contrast, anti-CD25 treatment only showed marginal improvement in efficacy when combined with immune checkpoint blockade (FIG. 3A). However, it should be noted that the anti-CD25 treatment may also affect activated Tells, which can transiently express CD25. As expected, without immune checkpoint blockade, both anti-CD25 and anti-Ly6G were ineffective (FIG. 3A).

To evaluate directly the ability of the tumor-induced G-MDSCs to interfere with the effects of immune checkpoint blockade, we isolated them from 4T1 tumor-bearing mice by affinity purification. We then injected the purified G-MDSCs into 4T1 tumor-bearing mice treated with anti-PD-1/anti-CTLA-4 antibodies plus AZA/entinostat. The adoptive transfer of G-MDSCs significantly attenuated the response to the combination therapy (FIG. 3C). Based on above results, we concluded that the effects of epigenetic modulation were more likely the result of depletion of G-MDSCs than of direct depletion of Tregs.

To investigate whether epigenetic modulation directly affected G-MDSCs, we purified these cells from 4T1 tumor-bearing mice as described above and treated them with entinostat or AZA in vitro. G-MDSCs showed markedly reduced viability after entinostat treatment in a dose-dependent fashion (FIG. 4A). Conversely, AZA had no effect at comparable concentrations (FIG. 4B). We also treated 4T1 tumor cells with the same concentrations of entinostat or AZA and found them unresponsive (FIGS. 4 A and B). Importantly, entinostat had only modest effects on $CD8^+$ T cells (FIG. 4A), creating a large therapeutic window in which G-MDSCs can be depleted while sparing $CD8^+$ T cells. Finally, we co-cultured $CD8^+$ T cells with G-MDSCs and analyzed the concentration of interferon-γ (IFN-γ) in culture medium by enzyme-linked immunosorbent assay (ELISA) following T cell activation with CD3 and CD28 antibodies. G-MDSCs inhibited IFN-γ secretion (FIG. 4C), whereas inclusion of entinostat in the culture medium reversed the inhibition in a dose-dependent manner (FIG. 4D). These data supported the notion that G-MDSCs directly inhibit the function of $CD8^+$ T cells and entinostat alleviates the inhibition by directly suppressing G-MDSCs.

To further confirm this conclusion, as well as to provide additional therapeutic approaches to achieve the same goal, we searched for other therapeutic agents that might suppress G-MDSC function. Phosphatidylinositide 3-kinases (PI3Ks) are known to play important roles in hematopoietic cell biology and can activate $Gr1^+/CD11b^+$ myeloid cells (26). We had previously developed a diverse array of PI3K inhibitors and chose to test one (J32) with high cellular potency (27-29). J32 proved to be cytotoxic to G-MDSCs at nanomolar concentrations ($EC_{50}$ of 14.3 nM) and much less toxic to $CD8^+$ T cells ($EC_{50}$ of 94.6 nM) (FIG. S4A). Treatment of 4T1 tumor-bearing mice with a relatively low dose of J32 (22 mg/kg) in combination with anti-PD-1/anti-CTLA-4 antibodies resulted in a marked reduction in circulating G-MDSCs (FIG. S4B) and eradication of 4T1 tumors in 80% of the animals (FIG. S4C). Alone, J32 had no appreciable effect on the 4T1 tumor growth.

Example 5

4T1 tumor cells were subcutaneously injected into BALB/c mice. On day 10, 12, 14 and 16 after the tumor cell injection, anti-PD-1 (10 mg/kg) and anti-CTLA-4 (10 mg/kg) antibodies were injected intraperitoneally into the mice in groups 2, 3, 4 and 5. On day 11, 13, 15 and 17, entinostat (ENT, 20 mg/kg) and 5-azacytidine (AZA, 0.8 mg/kg) were injected intraperitoneally into the mice in groups 4 and 5. On day 13 and 15, C. novyi-NT spores (50 million per mouse) were injected directly into the subcutaneous 4T1 tumors on mice in groups 1, 3 and 5. Mouse survival was then followed closely until day 100 after tumor cell injection. Survival curves are shown in FIG. 9. The dead mice dissected for pathological assessment invariably had extensive lung metastases.

The efficacy for checkpoint blockade (anti-PD-1/anti-CTLA-4) plus epigenetic inhibition (ENT/AZA) shown in this experiment (50% cure rate) was somewhat lower than that shown in the prior examples (80% cure rate). However, the efficacy for anti-PD-1/anti-CTLA-4 alone in this experiment was lower as well (10% cure rate here versus 30% in the prior examples). The efficacy enhancement observed in the combination therapy has not been diminished. The variation in efficacy is likely due to the quality of the antibodies from different manufacturing lots.

REFERENCES

The disclosure of each reference cited is expressly incorporated herein.
1. Korman A J, Peggs K S, & Allison J P (2006) Checkpoint blockade in cancer immunotherapy. Advances in immunology 90:297-339.
2. Pentcheva-Hoang T, Corse E, & Allison J P (2009) Negative regulators of T-cell activation: potential targets for therapeutic intervention in cancer, autoimmune disease, and persistent infections. Immunol Rev 229(1):67-87.
3. Pardon D M (2012) The blockade of immune checkpoints in cancer immunotherapy. Nat Rev Cancer 12(4):252-264.
4. Nagaraj S, Youn J I, & Gabrilovich D I (2013) Reciprocal relationship between myeloid-derived suppressor cells and T cells. J Immunol 191(1):17-23.
5. Chen L & Flies D B (2013) Molecular mechanisms of T cell co-stimulation and co-inhibition. Nature reviews. Immunology 13(4)227-242.
6. Talmadge J E & Gabrilovich D I (2013) History of myeloid-derived suppressor cells. Nat Rev Cancer 13(10): 739-752.
7. Lippitz B E (2013) Cytokine patterns in patients with cancer: a systematic review. Lancet Oncol 14(6):e218-228.
8. Zou W (2006) Regulatory T cells, tumour immunity and immunotherapy. Nature reviews. Immunology 6(4):295-307.
9. Hodi F S, et al. (2010) Improved survival with ipilimumab in patients with metastatic melanoma. N Engl J Med 363(8):711-723.
10. Topalian S L, et al. (2012) Safety, activity, and immune correlates of anti-PD-1 antibody in cancer. N Engl J Med 366(26)2443-2454.
11. Brahmer J R, et al. (2012) Safety and activity of anti-PD-L1 antibody inpatients with advanced cancer. N Engl J Med 366(26):2455-2465.
12. Wolchok J D, et al. (2013) Nivolumab plus ipilimumab in advanced melanoma. N Engl J Med 369(2):122-133.
13. Corbett T H, Griswold D P, Jr., Roberts B J, Peckham J C, & Schabel F M, Jr. (1975) Tumor induction relationships in development of transplantable cancers of the colon in mice for chemotherapy assays, with a note on carcinogen structure. Cancer Res 35(9)2434-2439.
14. Belnap L P, Cleveland P H, Colmerauer M E, Barone R M, & Pilch Y H (1979) Immunogenicity of chemically induced murine colon cancers. Cancer Res 39(4):1174-1179.
15. Dexter D L, et al. (1978) Heterogeneity of tumor cells from a single mouse mammary tumor. Cancer Res 38(10): 3174-3181.
16. Pulaski B A & O strand-Rosenberg S (1998) Reduction of established spontaneous mammary carcinoma metastases following immunotherapy with major histocompatibility complex class II and B7.1 cell-based tumor vaccines. Cancer Res 58(7):1486-1493.
17. Segal N H, et al. (2008) Epitope landscape in breast and colorectal cancer. Cancer Res 68(3):889-892.
18. Vogelstein B, et al. (2013) Cancer genome landscapes. Science 339(6127):1546-1558.
19. Rashid O M, et al. (2013) Resection of the primary tumor improves survival in metastatic breast cancer by reducing overall tumor burden. Surgery 153(6):771-778.
20. Lampen M H & van Hall T (2011) Strategies to counteract MHC-I defects in tumors. Current opinion in immunology 23(2):293-298.
21. Ostrand-Rosenberg S & Sinha P (2009) Myeloid-derived suppressor cells: linking inflammation and cancer. J Immunol 182(8):4499-4506.
22. Gabrilovich D I, Ostrand-Rosenberg S, & Bronte V (2012) Coordinated regulation of myeloid cells by tumours. Nature reviews. Immunology 12(4)253-268.
23. Couper K N, et al. (2009) Anti-CD25 antibody-mediated depletion of effector T cell populations enhances susceptibility of mice to acute but not chronic *Toxoplasma gondii* infection. J Immunol 182(7):3985-3994.
24. Setiady Y Y, Coccia J A, & Park P U (2010) In vivo depletion of CD4+FOXP3+ Treg cells by the PC61 anti-CD25 monoclonal antibody is mediated by FcgammaRIII+ phagocytes. Eur J Immunol 40(3):780-786.
25. Srivastava M K, et al. (2012) Myeloid suppressor cell depletion augments antitumor activity in lung cancer. PLoS One 7(7):e40677.
26. Schmid M C, et al. (2011) Receptor tyrosine kinases and TLR/IL1Rs unexpectedly activate myeloid cell PI3kgamma, a single convergent point promoting tumor inflammation and progression. Cancer Cell 19(6):715-727.
27. Schmidt-Kittler O, et al. (PI3Kalpha inhibitors that inhibit metastasis. Oncotarget 1(5):339-348.
28. Mandelker D, et al. (2009) A frequent kinase domain mutation that changes the interaction between PI3Kalpha and the membrane. Proc Natl Acad Sci USA 106(40): 16996-17001.
29. Zheng Z, et al. (2012) Definition of the binding mode of a new class of phosphoinositide 3-kinase alpha-selective inhibitors using in vitro mutagenesis of non-conserved amino acids and kinetic analysis. Biochem J 444(3):529-535.
30. Dokmanovic M, Clarke C, & Marks P A (2007) Histone deacetylase inhibitors: overview and perspectives. Mol Cancer Res 5(10):981-989.
31. Khan O & La Thangue N B (2012) HDAC inhibitors in cancer biology: emerging mechanisms and clinical applications. Immunology and cell biology 90(1):85-94.
32. Lyko F & Brown R (2005) DNA methyltransferase inhibitors and the development of epigenetic cancer therapies. J Natl Cancer Inst 97(20):1498-1506.
33. Griffiths E A & Gore S D (2008) DNA methyltransferase and histone deacetylase inhibitors in the treatment of myelodysplastic syndromes. Semin Hematol 45(1):23-30.
34. Baylin S B & Jones P A (2011) A decade of exploring the cancer epigenome-biological and translational implications. Nat Rev Cancer 11(10):726-734.
35. Wrangle J, et al. (2013) Alterations of immune response of non-small cell lung cancer with Azacytidine. Oncotarget 4(11):2067-2079.
36. Juergens R A, et al. (2011) Combination epigenetic therapy has efficacy in patients with refractory advanced non-small cell lung cancer. Cancer Discov 1(7):598-607.
37. Pulaski B A, Ostrand-Rosenberg S. Mouse 4T1 breast tumor model. Current protocols in immunology/edited by John E Coligan [et al]. 2001; Chapter 20:Unit 20 2.
38. Youn J I, Collazo M, Shalova I N, Biswas S K, Gabrilovich D I. Characterization of the nature of granulocytic myeloid-derived suppressor cells in tumor-bearing mice. Journal of leukocyte biology. 2012; 91:167-81.
39. Hamilton M J, Banath J P, Lam V, Lepard N E, Krystal G, Bennewith K L. Serum inhibits the immunosuppressive function of myeloid-derived suppressor cells isolated from 4T1 tumor-bearing mice. Cancer immunology, immunotherapy: CII. 2012; 61:643-54.

The invention claimed is:

1. A method of treating a tumor-bearing mammal, comprising:

administering entinostat which suppresses myeloid derived suppressor cells (MDSCs); and administering at least two antibodies comprising an anti-PD-1 antibody and an anti-CTLA-4 antibody which block two different immune checkpoints.

2. The method of claim 1 wherein:

(a) the tumor is not a non-small cell lung cancer (NSLC); or (b) spores of *Clostridium novyi*-NT are also administered to the tumor-bearing mammal.

3. The method of claim 1 wherein the tumor is selected from the group consisting of colorectal cancer, breast cancer, colorectal cancer metastasis, and breast cancer metastasis.

4. The method of claim 1 wherein entinostat is administered at a dose which is insufficient alone to inhibit tumor cell growth.

* * * * *